(12) United States Patent
Miller

(10) Patent No.: US 6,837,893 B2
(45) Date of Patent: Jan. 4, 2005

(54) MULTI-FASTENER SURGICAL APPARATUS AND METHOD

(75) Inventor: Arnold Miller, Chestnut Hill, MA (US)

(73) Assignee: Onux Medical, Inc., Hampton, NH (US)

( * ) Notice: Subject to any disclaimer, the term of this patent is extended or adjusted under 35 U.S.C. 154(b) by 59 days.

(21) Appl. No.: 09/944,841

(22) Filed: Aug. 31, 2001

(65) Prior Publication Data

US 2003/0105473 A1 Jun. 5, 2003

Related U.S. Application Data

(60) Provisional application No. 60/229,674, filed on Sep. 1, 2000.

(51) Int. Cl.[7] .............................................. A61B 17/04
(52) U.S. Cl. ...................................... 606/139; 606/151
(58) Field of Search ................................ 606/143, 139, 606/140, 142, 199, 232, 157, 158

(56) References Cited

U.S. PATENT DOCUMENTS

| | | |
|---|---|---|
| 4,366,819 A | 1/1983 | Kaster |
| 4,485,816 A | 12/1984 | Krumme |
| 4,665,906 A | 5/1987 | Jervis |
| 4,669,473 A | 6/1987 | Richards et al. |
| 5,002,563 A | 3/1991 | Pyka et al. |
| 5,067,957 A | 11/1991 | Jervis |
| 5,078,726 A | 1/1992 | Kreamer |
| 5,190,546 A | 3/1993 | Jervis |
| 5,219,358 A | 6/1993 | Bendel et al. |
| 5,258,000 A | 11/1993 | Gianturco |
| 5,259,394 A | 11/1993 | Bens |
| 5,540,701 A | 7/1996 | Sharkey et al. |
| 5,575,800 A | 11/1996 | Gordon |
| 5,582,616 A * | 12/1996 | Bolduc et al. ............... 606/143 |
| 5,597,378 A | 1/1997 | Jervis |
| 5,601,572 A | 2/1997 | Middleman et al. |
| 5,868,762 A | 2/1999 | Cragg et al. |
| 5,944,750 A | 8/1999 | Tanner et al. |
| 5,957,940 A | 9/1999 | Tanner et al. |
| 5,972,001 A * | 10/1999 | Yoon .......................... 606/139 |
| 5,984,917 A | 11/1999 | Fleischman et al. |
| 5,997,556 A * | 12/1999 | Tanner ........................ 606/153 |
| 6,113,611 A * | 9/2000 | Allen et al. .................. 606/151 |
| 6,132,438 A | 10/2000 | Fleischman et al. |
| 6,193,734 B1 | 2/2001 | Bolduc |
| 6,254,618 B1 | 7/2001 | Dakov |

(List continued on next page.)

FOREIGN PATENT DOCUMENTS

WO        WO 00/16701 A1     3/2000

OTHER PUBLICATIONS

U.S. Publication No. 0029048, published Mar. 7, 2002, by Miller.
U.S. Publication No. 0033005, published Feb. 13, 2003, by Houser et al.

Primary Examiner—Gary Jackson
(74) Attorney, Agent, or Firm—Pandiscio & Pandiscio

(57) ABSTRACT

A fastener preferably made from a shape memory alloy is provided which can access internal tissue or other synthetic material by catheter delivery through an endovascular pathway. After the fastener is deployed through layers of tissue or other material, it assumes a shape that automatically applies to the layers of tissue or other material an appropriate hemostatic compression which is relatively independent of tissue or material thickness. The fastener is a suitable replacement for conventional non bio-absorbable sutures and staples in certain clinical applications. The shape, method of deployment, and low force requirements make the disclosed apparatus suitable for endosurgical procedures where access to the wound site is limited. A method for deploying the fastener is also provided.

5 Claims, 26 Drawing Sheets

U.S. PATENT DOCUMENTS

| | | |
|---|---|---|
| 6,287,317 B1 | 9/2001 | Makower et al. |
| 6,306,141 B1 | 10/2001 | Jervis |
| 6,346,111 B1 | 2/2002 | Gordon et al. |
| 6,358,258 B1 | 3/2002 | Arcia et al. |
| 6,379,366 B1 | 4/2002 | Fleischman et al. |
| 6,416,522 B1 | 7/2002 | Strecker |
| 6,416,535 B1 | 7/2002 | Lazarus |
| 6,425,900 B1 * | 7/2002 | Knodel et al. .............. 606/139 |

* cited by examiner

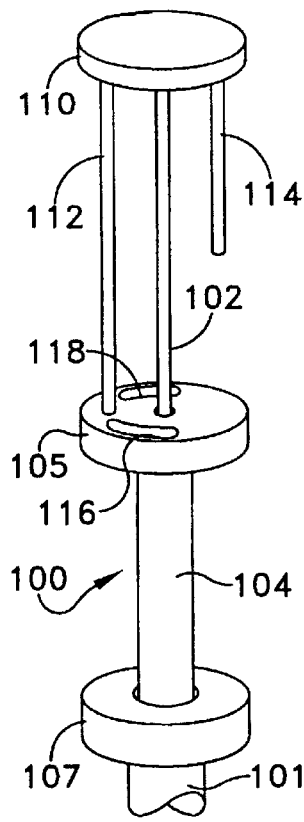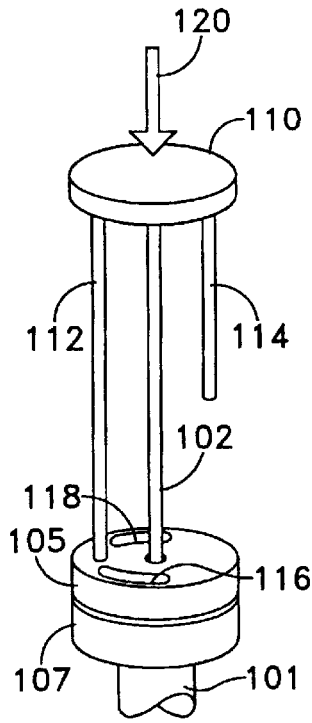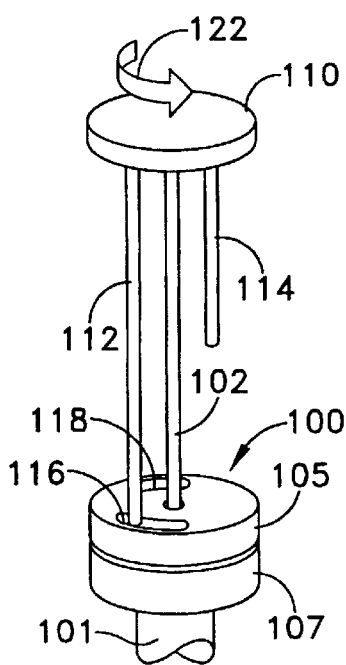
FIG. 6A	FIG. 6B	FIG. 6C
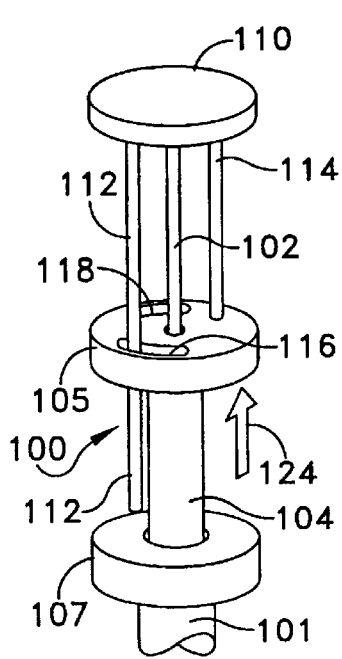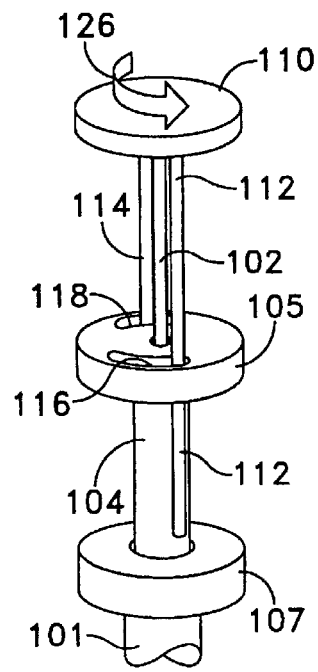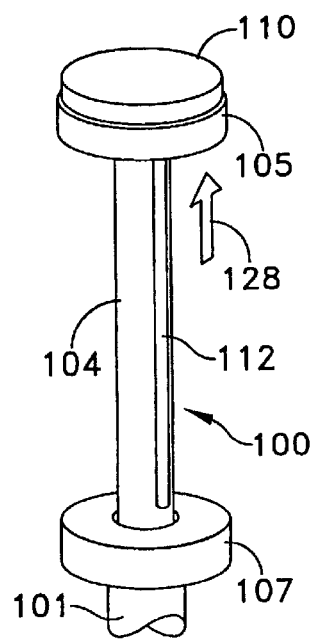
FIG. 6D	FIG. 6E	FIG. 6F

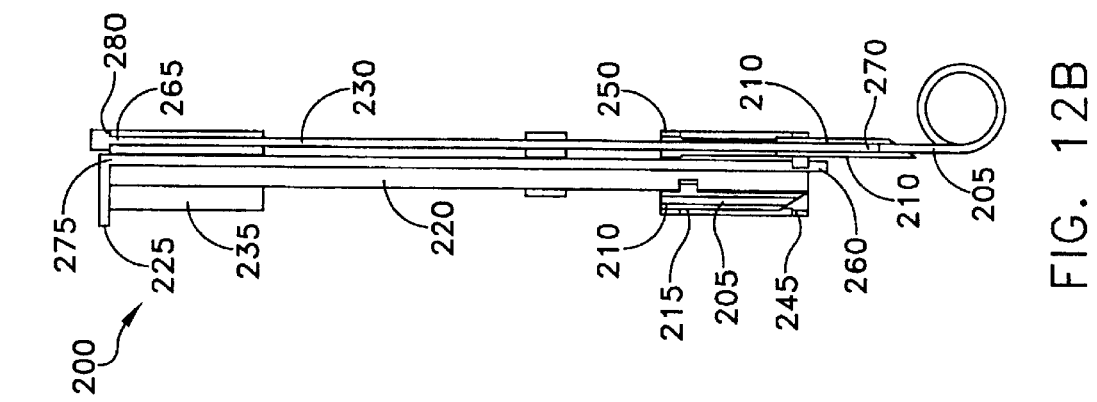
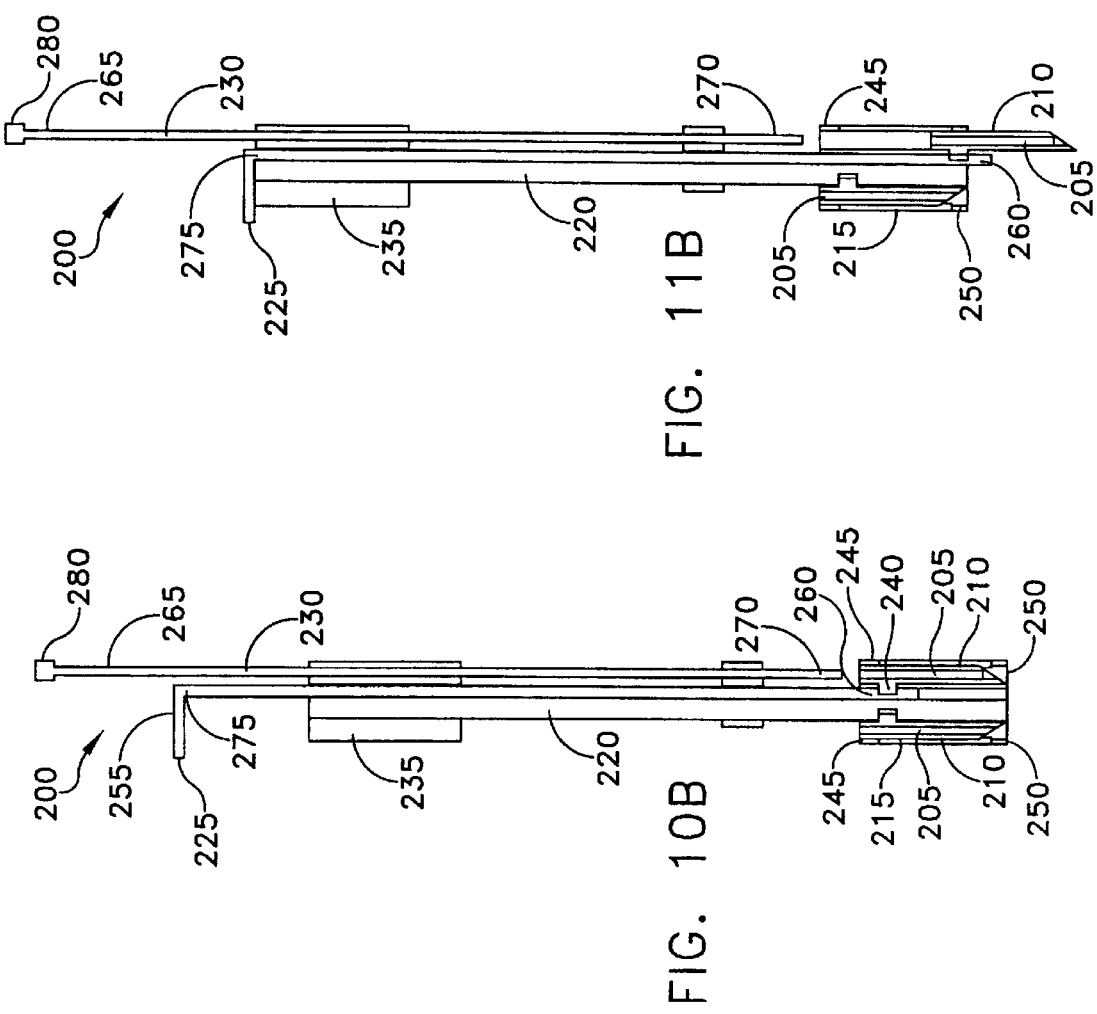

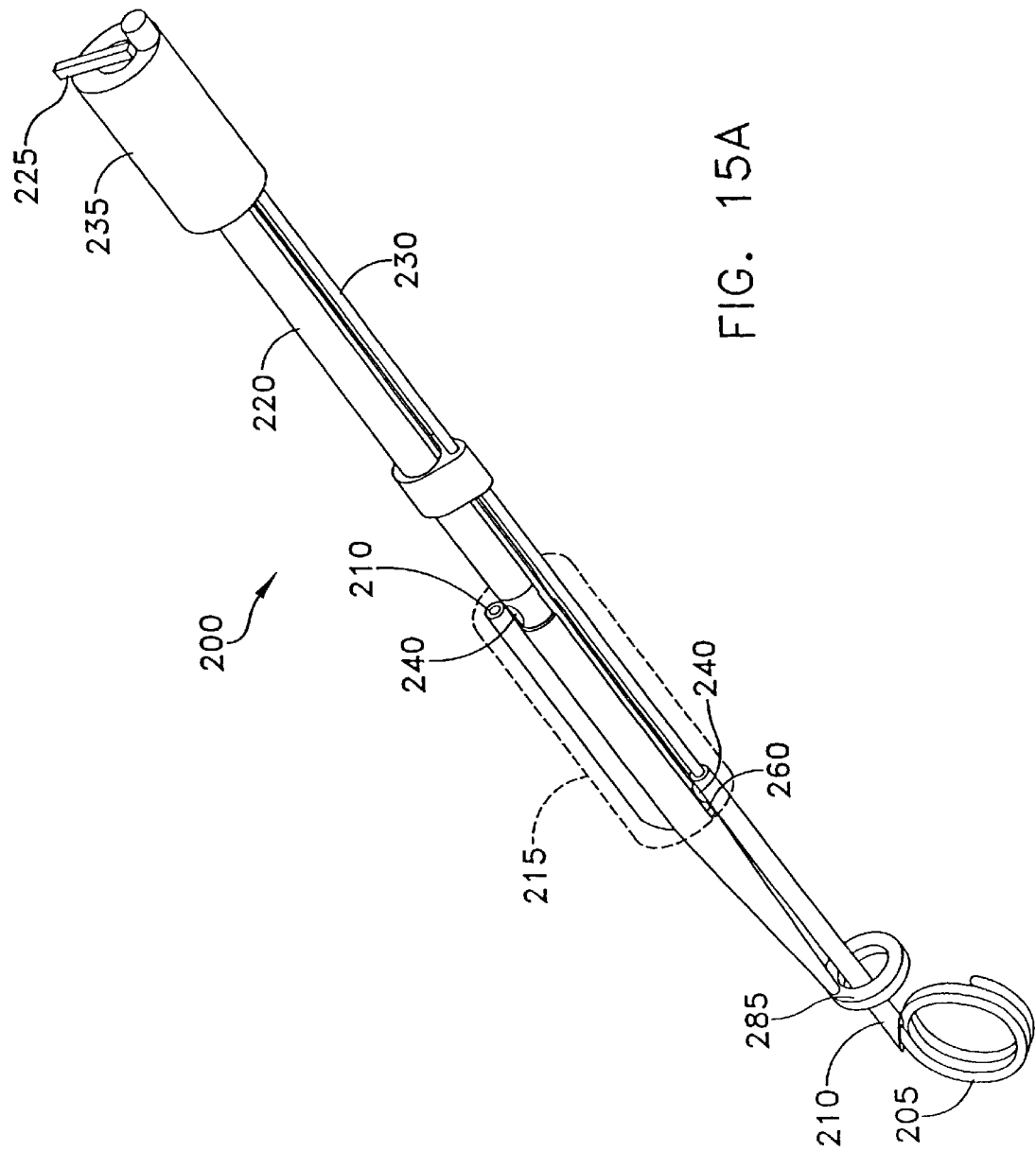

MULTI-FASTENER SURGICAL APPARATUS AND METHOD

REFERENCE TO PENDING PRIOR PATENT APPLICATION

This patent application claims benefit of pending prior U.S. Provisional Patent Application Ser. No. 60/229,674, filed Sep. 1, 2000 by Arnold Miller for HANDHELD FASTENER DEVICE FOR CARDIO-VASCULAR APPLICATIONS, which patent application is hereby incorporated herein by reference.

FIELD OF THE INVENTION

The invention related to a fastener and a deployment instrument for joining multiple layers of thin, flexible material. More particularly, the invention relates to a surgical fastener and a deployment instrument and method for joining living tissue and/or synthetic material which may be used as a substitute for tissue.

BACKGROUND OF THE INVENTION

Historically, living tissue has been most commonly surgically repaired by thread, such as a suture, introduced by a pointed metal needle and tied with just enough tension to establish hemostasis or control of bleeding by compressing the tissue. Correct tension is established by the surgeon based on observation and judgment derived from extensive training. Excess tension can cause necrosis (the localized death of living tissue) and eventual failure of the repair.

An alternate method of joining tissue using metal staples has evolved over the last 90 years to a point where specialized staples for both skin and internal tissue closure are in common use today. The staples, which have sharp points for penetrating tissue, are formed in place by delivery instruments which bend them to a permanent shape suitable for tissue retention. The delivery instruments include mechanisms, such as an anvil, which control to some extent the relationship between tissue and staple, including the compression necessary to control bleeding. To the extent that they do so, surgeon skill is less of a factor in successful wound closure.

For conventional surgery, the clinical results for suturing and stapling are essentially the same, but both have their disadvantages. Sutures are suitable for all types of wound closure, but require that the surgeon have adequate access to the wound site and possess the skill to choose and apply the suture correctly. Conventional staples can also be appropriate for internal use, but require that a strong, rigid anvil be placed behind the tissues to be joined. Furthermore, the application of staples requires that there be enough space for an instrument, which can produce the necessary force to form the staple against the anvil. Stapling, however, is generally faster and, as previously noted, requires a lower level of skill.

The recent development of a beneficial, less invasive technique for gall bladder removal has suggested the feasibility of other abdominal procedures, such as bowel and hernia repair, that require the remote application of an internal fastener. As a result, less invasive instruments have been developed for both suturing and stapling remotely from the wound site by the surgeon. At the same time, patient benefit considerations are driving the development of less invasive techniques for a full range of abdominal and thoracic procedures including coronary artery bypass and valve replacement.

To date, stapling has proven to be more suitable for less invasive surgery than suturing. Instruments developed for that purpose approximately replicate the functions of stapler developed for open surgery and are approximately as easy to use. Instruments developed for less invasive suturing, on the other hand, are slow and cumbersome and do not solve the essential problem of tensioning the suture and tying the knot remotely. Sutures will find limited use in less invasive surgery but it is most likely that related wound closure problems beyond the capability of conventional staples will be solved by innovative mechanical fasteners which can more easily be remotely applied.

For instance, a new fastener has been designed for a less invasive hernia repair in which a synthetic mesh is used to reinforce the repair by anchoring it to surrounding tissue. Suturing is feasible but difficult. Conventional stapling is not feasible because an anvil cannot access the distal side of the tissue. The new fastener has the shape of a coil spring with the wire sharpened at one end and has been used successfully to attach the mesh by screwing the coil through it into the tissue. This new fastener can access the wound site through a small port in the abdominal wall. This fastener, however, does not produce compression upon the synthetic and natural tissue layers and thus does not produce hemostasis because the fastener is screwed into the wound site in its natural shape. Because this fastener does not create hemostasis, it may not be suitable for a wide range of surgical applications.

Other surgical fasteners have been fabricated from shape memory alloy. U.S. Pat. No. 4,485,816 to Krumme discloses a shape-memory surgical staple that uses an electric current to heat the staple to make it close. U.S. Pat. No. 5,002,562 to Pyka et al. discloses a fastener made from shape memory alloy that has the shape of a suturing loop in its undeformed shape. As noted above, however, sutures and staples are not always desirable for all surgical applications.

It is believed that other applications exist or will be identified for fastening layers of tissue where anvil access is not practical and where compression must be applied to the tissue to achieve hemostasis. For example, these criteria apply to the attachment of a graft more or less at right angles to another, larger, blood vessel ("end to side" anastomosis) such as the aorta for vascular bypass purposes. The availability of a less invasive vascular bypass procedure implies a significant patient benefit. Another example is the use of the fastener in endovascular procedures to attach a graft within large vessels such as the aorta, iliac or femoral arteries to repair aneurysms and occlusions. Stents, which are currently used for this purpose, are often insufficiently compliant to prevent leakage and consequent failure of the repair. Direct fixation of the graft to the inner wall of the vessel by the fasteners described herein may overcome this inherent problem of current techniques for endovascular repair.

What is desired, therefore, is a mechanical fastener and deployment instrument that can access internal tissue through a small surgical access port or incision and that can be applied conveniently and remotely.

SUMMARY OF THE INVENTION

Accordingly, an object of the present invention is to provide a surgical fastener that can access internal tissue through a small surgical access port or incision.

It is a further object of the present invention to provide a surgical fastener that can be applied remotely.

It is yet another object of the present invention to provide a surgical fastener that uses the superelastic properties of a shape memory alloy without having to apply heat to the fastener.

It is still another object of the present invention to provide a deployment instrument that can be used to deploy the surgical fasteners of above.

These objects of the invention are achieved by a surgical fastener preferably made from a shape memory alloy that accesses internal tissue or other synthetic material through a small surgical access port or incision. After the fastener is deployed through layers of tissue, it assumes a shape that automatically applies to the layers of tissue an appropriate hemostatic compression which is relatively independent of tissue thickness. The fastener is a suitable replacement for conventional non bio-absorbable sutures and staples in certain clinical applications. Its shape, method of deployment and low force requirements make it suitable for standard surgical procedures and especially suitable for laparoscopic and other less invasive surgery where access to the wound site is limited including endovascular surgery. The invention is expected to be especially useful for attaching synthetic grafts to an aorta.

In one form of the invention, there is provided apparatus for inserting a surgical fastener through a plurality of portions of material, the apparatus comprising:

a surgical fastener having first and second ends and made from a material which enables the fastener to be transformed from a first stressed elongate shape to a second unstressed shape upon the release of the fastener from a stressed condition, the first stressed elongate shape of the fastener enabling the first end to be extended through a plurality of layers of material, and with the second shape of the fastener being in the form of a spring with a plurality of coils around a spring axis, with the coils being spring biased towards each other along the spring axis with sufficient axial force so as to enable coils on opposite sides of layers of material to clamp the layers of material together along the spring axis; and a single needle having first and second ends, penetration means adjacent the first end of the single needle, the penetration means being configured to pierce through the plurality of layers of material, and insertion means adjacent to the first end of the single needle, the insertion means being configured to place the surgical fastener through the plurality of layers of material pierced by the penetration means.

In another form of the invention, there is provided apparatus for inserting multiple surgical fasteners through a plurality of portions of material, the apparatus comprising:

a plurality of surgical fasteners, each of the surgical fasteners having first and second ends and made from a material which enables the fastener to be transformed from a first stressed elongate shape to a second unstressed shape upon the release of the fastener from a stressed condition, the first stressed elongate shape of the fastener enabling the first end to be extended through a plurality of layers of material, and with the second shape of the fastener being in the form of a spring with a plurality of coils around a spring axis, with the coils being spring biased towards each other along the spring axis with sufficient axial force so as to enable coils on opposite sides of layers to clamp the layers of material together along the spring axis;

a cartridge having a plurality of delivery tubes, the cartridge having first and second ends, each of the delivery tubes adapted to hold one of the surgical fasteners therein, each of the delivery tubes having first and second ends, the first end of the delivery tubes adapted to be slideably disposed from the first end of the cartridge, the first end of each of the delivery tubes having penetrating means to pierce through the plurality of layers of material;

a body in adjustable connection to the cartridge, the body having delivery tube control means and surgical fastener insertion means, the delivery tube control means being adapted to move the first end of each of the delivery tubes through the first end of the cartridge to pierce through the plurality of layers of material, the surgical fastener insertion means being adapted to place the surgical fastener through the plurality of layers of material pierced by the penetrating means of each of the delivery tubes; and means for moving the cartridge with respect to the body to sequentially align one of the delivery tubes having one of the surgical fasteners of the cartridge with the delivery tube control means and the surgical fastener insertion means of the body, wherein the plurality of surgical fasteners is sequentially placed without reloading after each placement.

In another form of the invention, there is provided a method for inserting a surgical fastener through a plurality of portions of material, the method comprising:

providing apparatus for inserting a surgical fastener through a plurality of portions of material, the apparatus comprising:

a surgical fastener having first and second ends and made from a material which enables the fastener to be transformed from a first stressed elongate shape to a second unstressed shape upon the release of the fastener from a stressed condition, the first stressed elongate shape of the fastener enabling the first end to be extended through a plurality of layers of material, and with the second shape of the element being in the form of a spring with a plurality of coils around a spring axis, with the coils being spring biased towards each other along the spring axis with sufficient axial force so as to enable coils on opposite sides of layers to clamp the layers of material together along spring axis; and a single needle having first and second ends, penetration means adjacent the first end of the single needle, the penetration means being configured to pierce through the plurality of layers of material, and insertion means adjacent to the first end of the single needle, the insertion means being configured to place the surgical fastener through the plurality of layers of material pierced by the penetration means;

placing the single needle adjacent the plurality of layers of material, with the surgical fastener being configured in the first stressed elongate shape;

penetrating the plurality of layers of material with the penetration means of the single needle, the penetration of the plurality of layers of material being performed at the first end of the single needle;

inserting a first portion of the surgical fastener through the plurality of layers of material using the insertion means; and withdrawing the penetration means of the single needle from the plurality of layers of material, wherein a second portion of the surgical fastener is positioned on the opposite side of the plurality of layers of material from the first portion of the surgical fastener so as to enable coils on the opposite sides of the layers to clamp the material together.

In yet another form of the invention, there is provided a method for inserting a surgical fastener through a plurality of portions of material, the method comprising:

providing apparatus for inserting multiple surgical fasteners through a plurality of portions of material, the apparatus comprising:

a plurality of surgical fasteners, each of the surgical fasteners having first and second ends and made from a material which enables the fastener to be transformed from a first stressed elongate shape to a second unstressed shape upon the release of the fastener from a stressed condition, the first stressed elongate shape of the fastener enabling the first end to be extended through a plurality of layers of material, and with the second shape of the element being in the form of a spring with a plurality of coils around a spring axis, with the coils being spring biased towards each other along the spring axis with sufficient axial force so as to enable coils on opposite sides of layers to clamp the layers of material together along spring axis;

a cartridge having a plurality of delivery tubes, the cartridge having first and second ends, each of the delivery tubes adapted to hold one of the surgical fasteners therein, each of the delivery tubes having first and second ends, the first end of the delivery tubes adapted to be slideably disposed from the first end of the cartridge, the first end of each of the delivery tubes having penetrating means to pierce through the plurality of layers of material;

a body in adjustable connection to the cartridge, the body having delivery tube control means and surgical fastener insertion means, the delivery tube control means being adapted to move the first end of each of the delivery tubes through the first end of the cartridge to pierce through the plurality of layers of material, the surgical fastener insertion means being adapted to place the surgical fastener through the plurality of layers of material pierced by the penetrating means of each of the delivery tubes; and means for moving the cartridge with respect to the body to sequentially align one of the delivery tubes having one of the surgical fasteners of the cartridge with the delivery tube control means and the surgical fastener insertion means of the body, wherein the plurality of surgical fasteners is sequentially placed without reloading after each placement;

placing the first end of the cartridge adjacent the plurality of layers of material, with the surgical fastener being configured in the first elongate shape;

penetrating the plurality of layers of material with the first end of the delivery tube using the delivery tube control means;

inserting a first portion of the surgical fastener through the plurality of layers of material using the surgical fastener insertion means;

withdrawing the first end of the cartridge from the plurality of layers of material using the delivery control means; and moving the cartridge with respect to the body to sequentially align the delivery tubes having one of the surgical fasteners of the cartridge with the delivery tube control means and the surgical fastener insertion means of the body, wherein the plurality of surgical fasteners are sequentially placed without reloading after each placement.

The above and other features of the invention, including various novel details of construction and combinations of parts and method steps, will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 6A–6F are front isometric views of another embodiment of a deployment instrument showing the insertion of a surgical fastener;

FIGS. 10A–12A are views like those of FIGS. 10–12, except showing the cartridge in a semitransparent form;

FIGS. 10B–12B are views like those of FIGS. 10–12 and 10A–12A, except that they are shown in side view;

FIGS. 13A–15A are views like those of FIGS. 13–15, except showing the cartridge in a semitransparent form;

FIGS. 13B–15B are views like those of FIGS. 13–15 and 13A–15A, except that they are shown in side view;

DETAILED DESCRIPTION OF THE PREFERRED EMBODIMENTS

Surgical fasteners, each in accordance with the invention, are shown in FIGS. 1A–4. The surgical fastener is preferably a one piece metal or plastic element appropriately configured during manufacture to hold layers of tissue in compression. To apply the fastener, as shown in FIGS. 5A–5F, 6A–6F, and 9A–9D, a straight tube or needle included in a delivery mechanism is preferably used to hold and deflect the fastener from its final shape into a straight configuration. In application, the tube is either inserted through the tissue or held against the tissue to be joined and the fastener is pushed from the tube until the fastener penetrates the tissue and gradually assumes its original shape, trapping and compressing the layers of tissue 18 between its various elements.

In order to straighten the various surgical wire fasteners described herein without permanent deformation, a superelastic alloy of nickel and titanium is preferably used to make the fasteners. The fastener is preferably made from a commercial material Nitinol, which is referred to as a "shape memory alloy." Superelasticity can be conveniently likened to memory. Although forced into a straight line after forming, the superelastic fastener is able to "remember" its former shape and to return to it when no longer constrained within a straight tube. Nitinol in superelastic form has an extremely high elastic limit, which allows large amounts of bending without permanent deformation. In general, Nitinol is capable of strain ratios of up to 8% without experiencing permanent deformation. For round wire, the fastener is designed to function within the limits of d/2R equal to or less than 0.08, where d is the diameter of the wire and R is the radius to which the wire is formed. It should be noted that the fastener described herein can be made from any material so long as it is adequately elastic. Preferably, the material has superelastic characteristics.

Figure 1A:
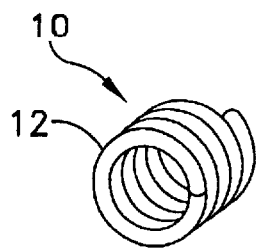
FIGS. 1A, 1B and 1C are an isometric view and two side views, respectively, of the first embodiment of the surgical fastener in accordance with the invention.
Figure 1B:
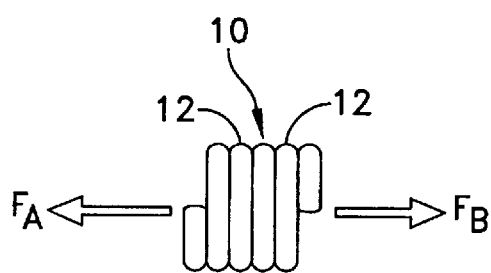
Figure 1C:
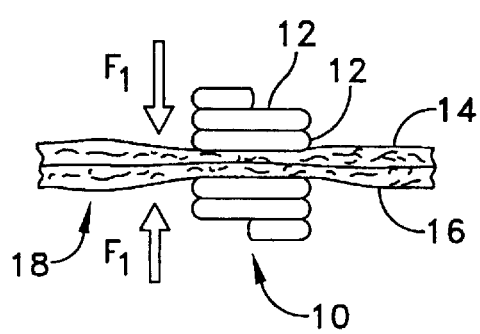

The preferred embodiment of the fastener 10, shown in FIGS. 1A–1C, is essentially that of the body of an extension spring having coils 12. At rest, the coils of this fastener 10 are spring biased towards each other so that a force $F_A$ is required to effect separation of the coils. The force at which the coils just begin to separate is the preload value for the fastener. Additional force causes separation of the coils 12 as a function of the gradient of the fastener. Shown in FIG. 1C, layers of tissue 18 that are trapped between adjacent coils 12 of the fastener will be clamped with a force F1 being substantially normal to the surface of the tissue 18 and having a value somewhat higher than the preload value of the fastener. This force, which is a function of fastener material, dimensions and winding technique, is chosen to insure hemostasis when vascular tissue is to be clamped. It should be noted that a compression spring could be used in place of an extension spring so long as the tissue is thick enough that it is compressed between the coils of the fastener once it is in place. The theory and practice of winding preloaded coils of metallic wire is routinely practiced in the manufacture of extension springs and is well known to those skilled in the art.

When the fastener of FIGS. 1A–1C is made of a superelastic material and the strain ratio limitation described above is observed, the fastener can be straightened to penetrate tissue 18 and then released to allow its coils to reform on both the proximate 14 and distal 16 sides of the tissue thereby clamping the tissue between two coils. The number of coils 12 is not especially critical. At least two full coils 12 are required and more, such as four coils, are preferable to make placement in the tissue less critical. The coils 12 preferably have a diameter of 3/16 to 1/4 of an inch. Preferably, the end of the fastener inside of the body rests flush next to the adjacent coil so that the body will not be injured from the fastener end.

Figure 2:
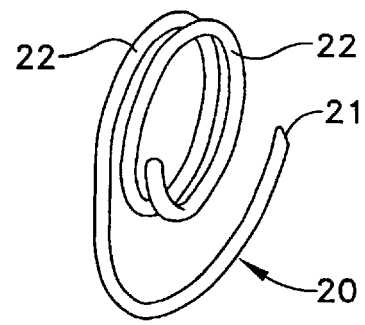
FIG. 2 is an isometric view of the second embodiment of the surgical fastener in accordance with the invention.
Figure 3:
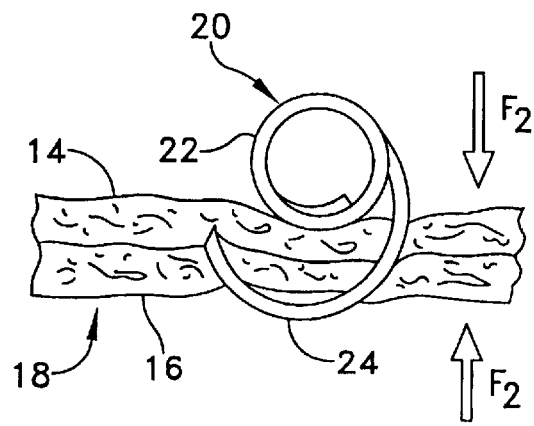
FIG. 3 is a side cutaway view of the second embodiment of the surgical fastener of FIG. 2 in accordance with the invention.

FIGS. 2 and 3 show another embodiment of the fastener 20 before and after installation in two layers 14, 16 of tissue 18. The presence of the tissue layers prevents the fastener from returning completely to its original state. The force required to spread the spring biased fastener apart by this amount therefore also represents the substantially normal compressive force $F_2$ applied to the layers of tissue 18. That force, which is a function of wire diameter and fastener geometry, is chosen by design to achieve homeostasis. Those parameters also determine the gradient or stiffness of the fastener as measured in terms of force $F_2$ versus deflection of the fastener. Since different tissue thicknesses produce different deflections, and therefore different compressive forces, the gradient must be sufficiently low to maintain reasonable hemostasis over the normal range of tissue thickness without inducing necrosis.

FIG. 2 is an isometric view of the fastener 20 shown schematically in FIG. 3. The lower coil 24 penetrates the tissue and curves in a half circle to re-enter the tissue layers. The upper coils 22 bear on the tissue and tend to trap it inside of the larger lower coil. The number of upper coils 22 can vary without altering the essential behavior of the fastener 20. Preferably, two or more coils 22 are used to help distribute clamping forces more uniformly about the lower coil thereby preventing mis-orientation of the fastener 20 in the tissue 18.

Figure 4:
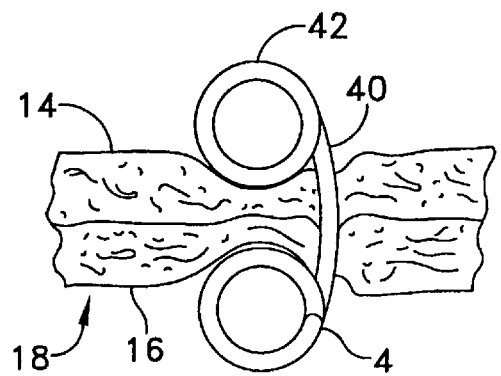
FIG. 4 a side cutaway view of the third embodiment of the surgical fastener in accordance with the invention.

The fastener 40 in FIG. 4 has symmetrical coils 42 to distribute stress uniformly on both sides of the tissues to be joined.

The fasteners in FIGS. 2–3 and 4 are similar to the fastener in FIGS. 1A–1C in that they are spring biased and use coils to apply pressure. The coils in FIGS. 2–3 and 4 each have an axis that is oriented substantially transverse to the direction that the fastener takes when it is in a straightened form, whereas the coils in FIGS. 1A–1C each have an have an axis that is substantially transverse to its straightened form.

The fasteners in FIGS. 1C, 3 and 4 all show a fastener clamping two layers of living tissue 18 which include a proximal layer 14 and a distal layer 16 of tissue. The fasteners described herein, however, can fasten any type of materials together, such as a graft or synthetic fibers which may be used as a substitute for tissue, or a combination thereof. The synthetic fibers, for example, may be a material such as Gore-Tex, Dacron or Teflon. Autogenous and non-autogenous human tissue, as well as animal tissue, may also be used.

For all fasteners described above, the leading end 21 of the fastener, shown in FIG. 2, can be sharpened for ease of penetration either by cutting the wire on a bias or by tapering the end to a sharp point during manufacture of the fastener. The bias cut is commonly used to make sharp points on conventional staples and taper pointing is used to make a certain class of suture needles. Both techniques are well known to those skilled in the art. Other sharpening techniques such as trocar points may also be effectively applied to the fastener. Alternatively or additionally, a tube 154 of a deployment instrument 150 that houses the fastener, as shown in FIGS. 9A–9D, can have a sharpened tip which is used to penetrate the tissue 18 prior to pushing the fastener from said tube.

A wide variety of fasteners can be designed within the scope of this invention for an equally wide variety of fastening purposes. Some of these shapes are shown in FIGS. 1A–4 and it should be apparent that other variations are both possible and likely as the invention becomes more widely applied.

The surgical fasteners described herein can also be used in applications that require the insertion of a fastener from the interior. For example, the fasteners can be used in endovascular procedures to attach a graft within large vessels such as the aorta or iliac arteries to repair aneurysms or occlusions.

Figures 5A, 5B, 5C:
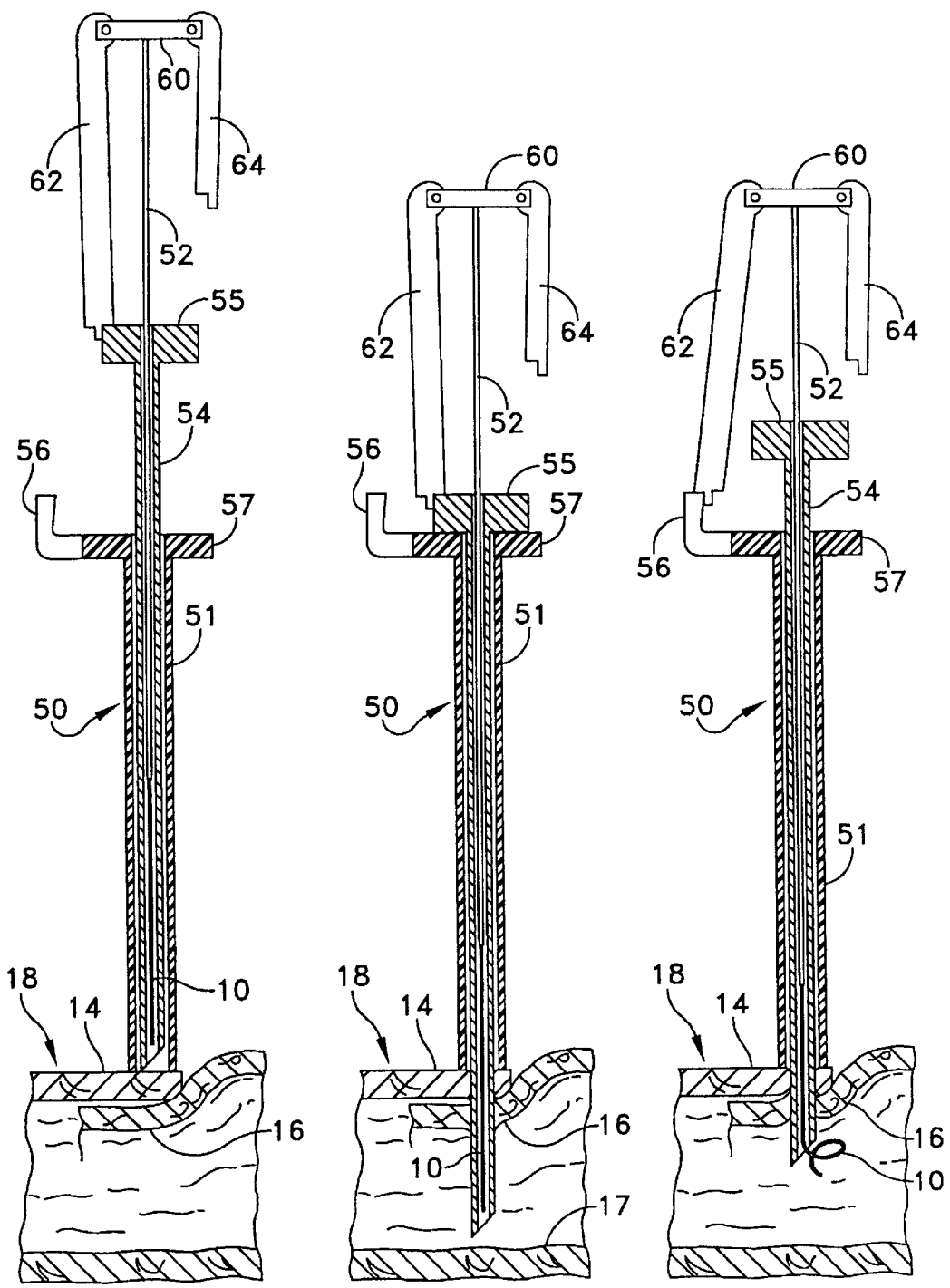
FIGS. 5A–5F are front cutaway views of a deployment instrument showing the insertion of the surgical fastener of FIG. 1.

FIGS. 5A–5F show a first embodiment of a deployment instrument 50 and the method for inserting the fastener. The deployment instrument 50 consists of a plunger 52 having a head portion 60, a needle 54 having a head portion 55, and a sleeve 51 having a head portion 57 and a stop 56. The plunger 52 fits slidingly inside a lumen of the needle 54, which fits slidingly inside of the sleeve 51. FIGS. 5A–5F show the fastener 10 being used to attach a graft 16 to a blood vessel having a first layer of tissue 14 and an opposite wall 17 (FIG. 5B). The fasteners described herein, however, can be used for any layers of material or tissue. Furthermore, the deployment instrument 50 can deliver any of the fasteners described herein.

Depending on the situation, support for the lower membrane 16 will be required in order to insert the fastener 10. This normally will be the rigidity of the body tissue itself or a mechanical support which is provided separately, often as an integral part of the instrument that deploys the graft.

For the deployment instrument shown in FIGS. 5A–5D, the head portion 60 of the plunger 52 has two stops 62, 64 attached to it. One of the stops 62 pivotally engages the head portion 55 of the needle 54 and also pivotally engages a stop 56 of the head portion 57 of the sleeve 51. The other stop 64 can engage the head portion 55 of the needle 54. These stops 62, 64 are used to control the amount of depth that the needle and/or fastener may be inserted into the tissue 18.

In FIG. 5A, the deployment instrument is shown ready to insert a fastener 10 into layers of tissue 18 with the tip of the instrument 50 placed against the tissue. First, the stop 62 is engaged against the head portion 55 of the needle 54, such that the needle 54 and plunger 52 can be inserted into the tissue 18 in unison. The needle 54 and plunger 52 are inserted until the head portion 55 of the needle 54 rests upon the head portion 57 of the sleeve 51, as shown in FIG. 5B. It should be apparent that if the needle is inserted into a blood vessel, as shown in FIGS. 5A–5D, care should be taken not to insert the needle past the opposite wall 17 of the vessel.

In FIG. 5C, the stop 62 is swung to engage the stop 56 on the sleeve 51. This will enable the needle 54 to be raised while the plunger 52 remains still. While the needle 54 is withdrawn, the restraining force of the needle 54 upon the fastener 10 is removed and the fastener begins to form in its unstressed and undeformed shape.

Figures 5D, 5E, 5F:
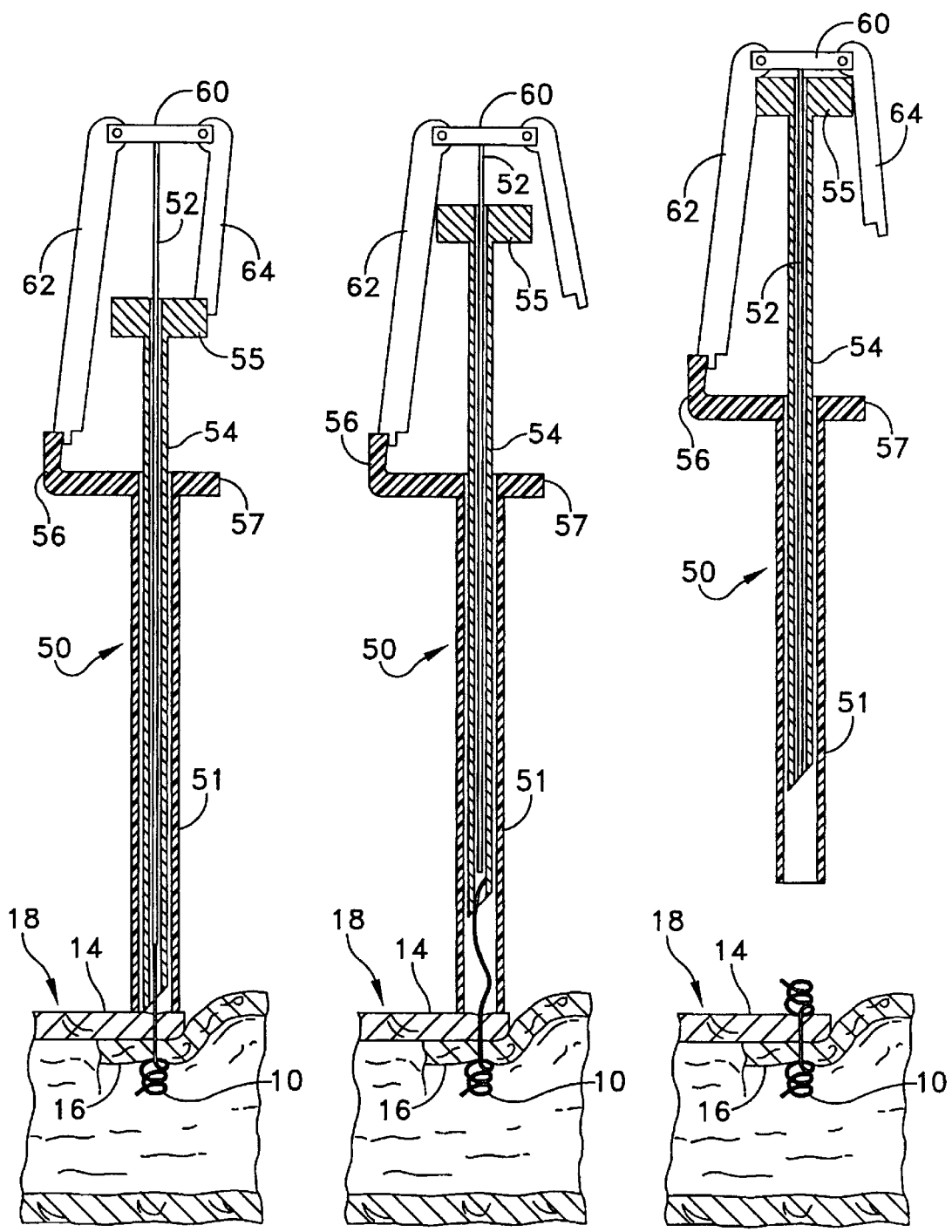

In FIG. 5D, the needle 54 is raised until its head portion 55 engages stop 64. When the needle head portion 55 engages stop 64, a doctor can be certain that the needle has exited the layers of tissue 18. The lower portion of fastener 10 will now have formed itself in the shape of a coil.

In FIG. 5E, the stop 64 is swung away from the head portion 55 such that the needle 54 can be withdrawn fully. As shown, the fastener 10 begins to form in its unstressed shape as the needle 54 is removed.

FIG. 5F shows the full withdrawal of the deployment instrument 50. The fastener 10 can now fully assume its unstressed shape. It should be noted that the unstressed coils of the fastener 10 shown in FIGS. 5D through 5F are shown having an exaggerated shape for the sake of clarity. The fastener 10 more accurately would appear as shown in FIG. 1C with the coils exerting a compressive pressure upon the layers of tissue 18.

FIGS. 6A through 6F show a second embodiment of deployment instrument 100 which can deliver any of the fasteners described herein. A plunger 102 has a head portion 110 having both a short stop 114 and a long stop 112 attached to it. A head portion 105 of a needle 104 has two slots 116 and 118 to accept the long and short stops 112, 114, respectively, at different times of the process. The needle 104 is slidingly accepted by a sleeve 101 having a head portion 107. The tip of the deployment instrument 100, fastener 10 and needle 104 for FIGS. 6A–6F appear the same as in FIGS. 5A–5F, respectively, and are not shown for the sake of clarity.

First, as shown in FIG. 6A, the long stop 112 is brought into contact with the head portion 105 of the needle 104. The plunger 102 and needle 104 are then inserted into the tissue in unison by pushing down in the direction of arrow 120 until the needle's head portion 105 comes into contact with the sleeve's head portion 107, as shown in FIG. 6B. The needle 104 and fastener have penetrated the layers of tissue.

The head portion 110 of the plunger 102 is then rotated as shown in FIG. 6C in the direction of arrow 122 until the long stop 112 can be inserted into slot 116. The needle's head portion 105 is then raised in the direction of arrow 124 (FIG. 6D) until the needle's head portion 105 comes into contact with the short stop 114, as shown in FIG. 6D. In FIG. 6D, the needle 104 will be fully withdrawn from the layers of tissue.

In FIG. 6E, the plunger's head portion 110 is rotated in the direction of arrow 126 until the short stop 114 can be inserted into slot 118. The needle's head portion 105 is then fully raised in the direction of arrow 128 (FIG. 6F) until the head portion 105 comes into contact with the plunger's head portion 110. The needle 104 is now fully retracted from the fastener which should be fastened in the tissue and formed in its unstressed state.

It should be apparent that many types of stops could be used to position the needle 54, 104 and plunger 52, 102 of the deployment instruments 50 and 100. For example, the needle could function with only a single stop attached to the shaft of the plunger. Alternatively, visual indicators could be used, but would be inherently less reliable. It should be apparent that the delivery instruments shown in FIGS. 5A–5F and 6A–6F could function properly without the short stops 64, 114, but not as reliably. Also, the delivery instruments, as shown in FIGS. 5A–5F and 6A–6F, could function without the sleeve 51 or 101, respectively. It should be apparent that a plurality of any of these deployment instruments described herein could be integrated in a single deployment instrument for sequential or simultaneous deployment of the fastener.

Figure 7:
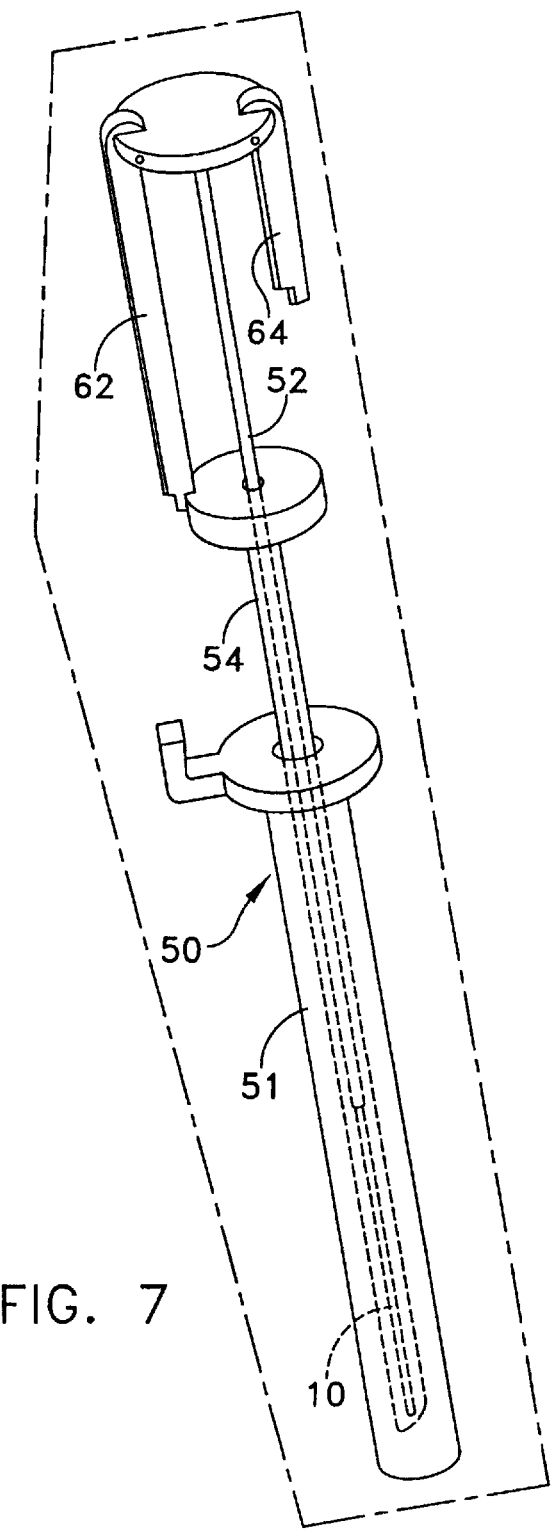
FIG. 7 is a front isometric view of the deployment instrument of FIGS. 5A–5F as it is shipped.

FIG. 7 shows the deployment instrument 50 as it might be shipped from a manufacturer. The surgical fastener 10 preferably is already inserted and straightened inside of the needle 54 for ease of use. The deployment instrument 50 can be shipped with or without the sleeve 51, which can be added later when the fastener is ready to be inserted.

Figure 8:
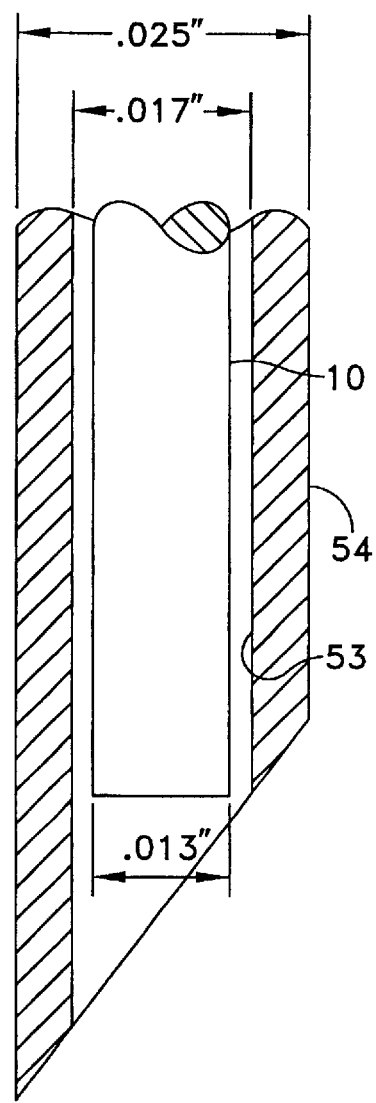
FIG. 8 is a front cutaway view of the deployment instruments of FIGS. 5A–5F and 6A–6F.

FIG. 8 shows an enlarged view of the needle of either FIGS. 5A–5F or 6A–6E with a fastener inside of it. A typical aspect ratio of the length to diameter for this device can be in the order of 40 or 50 for less invasive use. The diameter of the fastener is preferably between 0.012 to 0.014 of an inch, more preferably its diameter is 0.013 of an inch, the inside diameter of a lumen 53 of the needle 54 is preferably 0.017 of an inch and the outside diameter of the needle is preferably 0.025 of an inch.

FIGS. 9A–9D show a third embodiment of the deployment instrument 150 and the method for inserting the fastener. The third embodiment of the deployment instrument 150 is different from the first two embodiments in that a restraining tube 154 is not sharpened to penetrate tissue. Thus, the surgical fastener 20 used with the deployment instrument 150 should have a sharpened end to penetrate tissue. The deployment instrument 150, consisting of slender tubes and rods, is inherently small in diameter compared to its length. Thus, FIGS. 9A–9D are illustrated with a much less favorable aspect ratio for the sake of clarity. A typical aspect ratio of the length to diameter for this device can be in the order of 40 or 50 for less invasive use. It should be apparent that other ergonomically sophisticated designs for the deployment instrument 150 can be envisioned and realized. It should also be apparent that several of these deployment instruments could be integrated in a single deployment instrument 150 for sequential or simultaneous deployment of the fastener.

Figure 9:
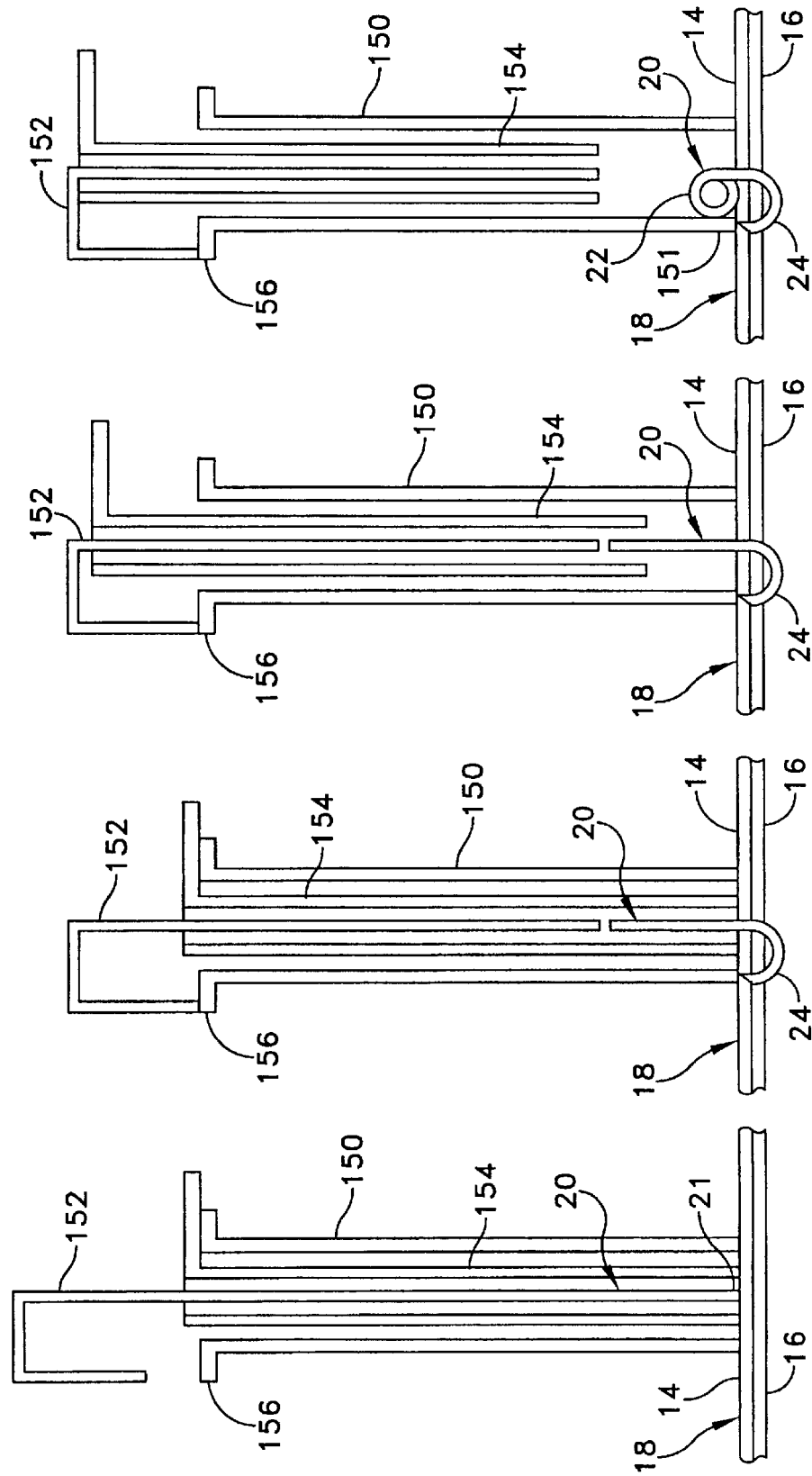
FIGS. 9A–9D are side cutaway views showing the use of a deployment instrument with the surgical fastener of FIG. 2.

FIG. 9A shows a deployment instrument 150 resting on layers of tissue 18 to be joined. The deployment instrument 150 restrains a fastener by placing stress upon it. The fastener 20, which in this example is the fastener of FIG. 1, resides in a substantially straightened form entirely within the restraining tube 154. It should be apparent that any of the fasteners described herein if given a pointed end 21 can be used with the deployment instrument of FIGS. 9A–9D. The pointed end 21 of the fastener 20 is facing toward the tissue. A plunger 152 rests on the fastener 20 and is configured to push the fastener partially out of the restraining tube 154 until the plunger 152 stops against a shield 156 as shown in FIG. 9B.

FIG. 9B shows the fastener 20 partially installed by the plunger 152. As the fastener emerges from its restraining tube, the fastener 20 penetrates the proximal 14 and distal 16 layers of tissue and gradually assumes the remembered shape of its lower coil, piercing the distal tissue layer 16 again as it turns upward. The lower coil 24 of the fastener 20, however, preferably remains substantially on the distal side of the tissue. At this point, plunger 152 bears on the shield 156 and can progress no further. Depending on the clinical application, it may be necessary to support the tissue 18 distally during penetration.

FIG. 9C shows restraining tube 154 moving upward, gradually freeing the fastener 20 to assume its remembered shape. It will obviously not be able to do so until the restraining tube 154 is completely clear, which happens when the restraining tube stops against plunger 152. The restraining tube 154 tends to pull the fastener 20 out of the tissue due to friction producing forces exerted by the fastener on the restraining tube as the former tries to assume its remembered shape. This tendency is offset by the plunger 152 bearing on the upper end of the fastener 20 as the restraining tube 154 moves upward.

FIG. 9D shows restraining tube 154 in its fully upward position as determined by the plunger 152. The restraining tube 154 has cleared the fastener 20 and allowed it to assume its remembered, coiled shape 22, bearing against the tissue 18. The fastener 20 forms within a guide tube 151, suggesting that the guide tube 151, properly shaped, may serve to guide the fastener 20 as it forms above the tissue 18. This may be a useful feature, especially for more complex fasteners which may re-form incorrectly when released from constraint.

The guide tube 151 can serve a dual function as described above, providing a reference stop for plunger 152 and a forming guide for the fastener 20. In some cases the guide tube 151 will not be required.

Figure 10:
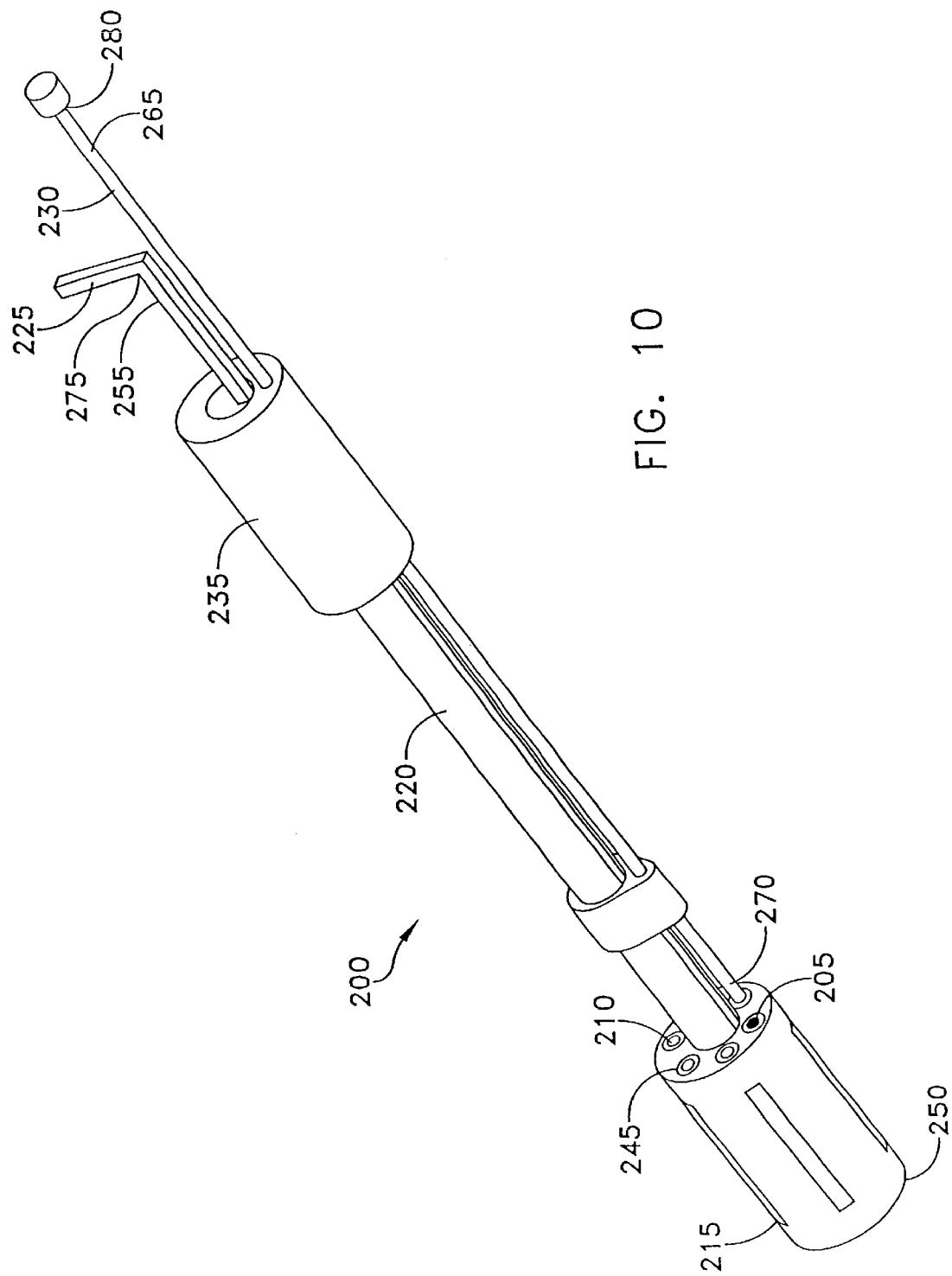
FIGS. 10–12 are perspective views showing use of a multi-suture deployment apparatus with the surgical fastener of FIG. 2.
Figure 10A:
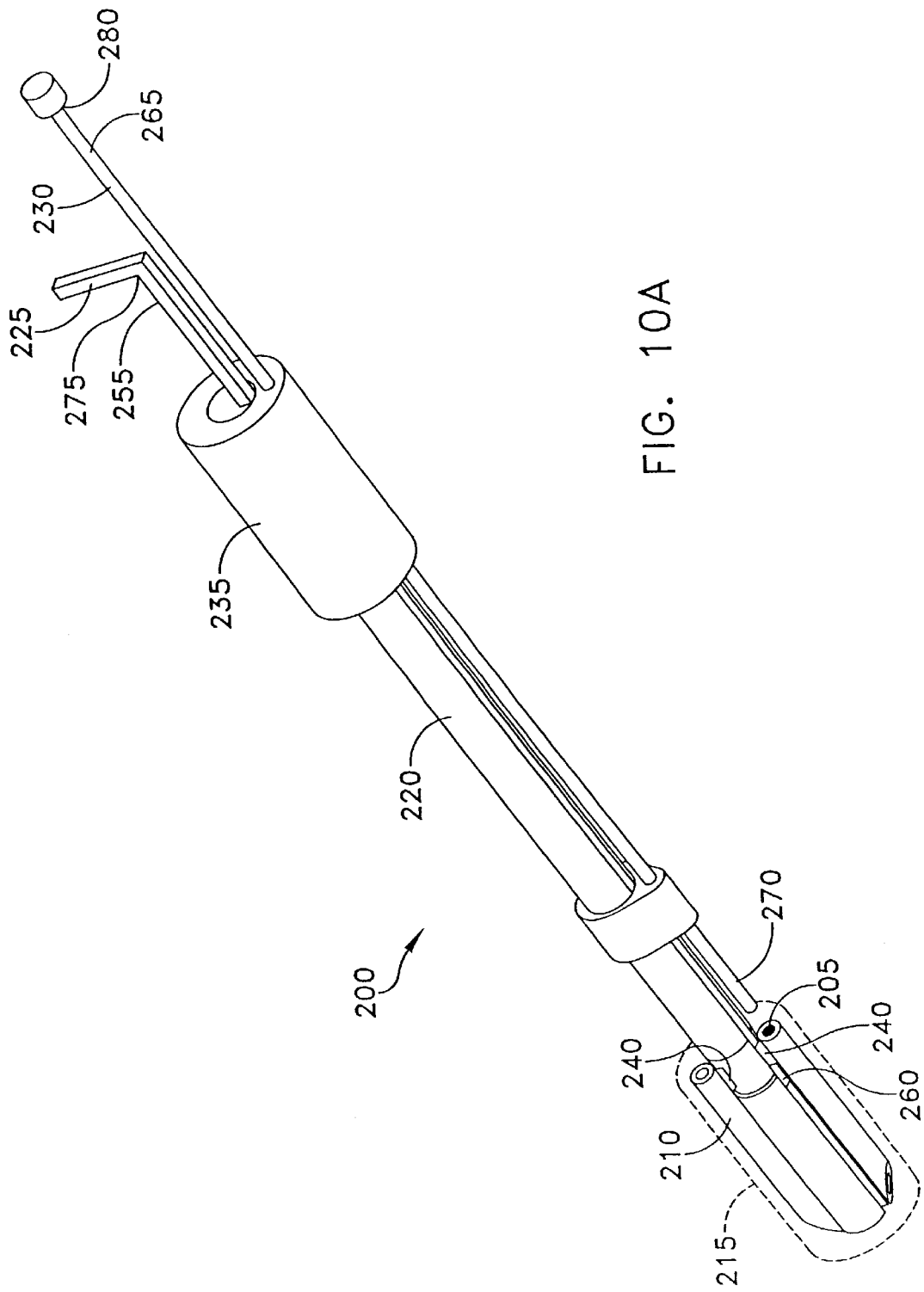
Figure 11:
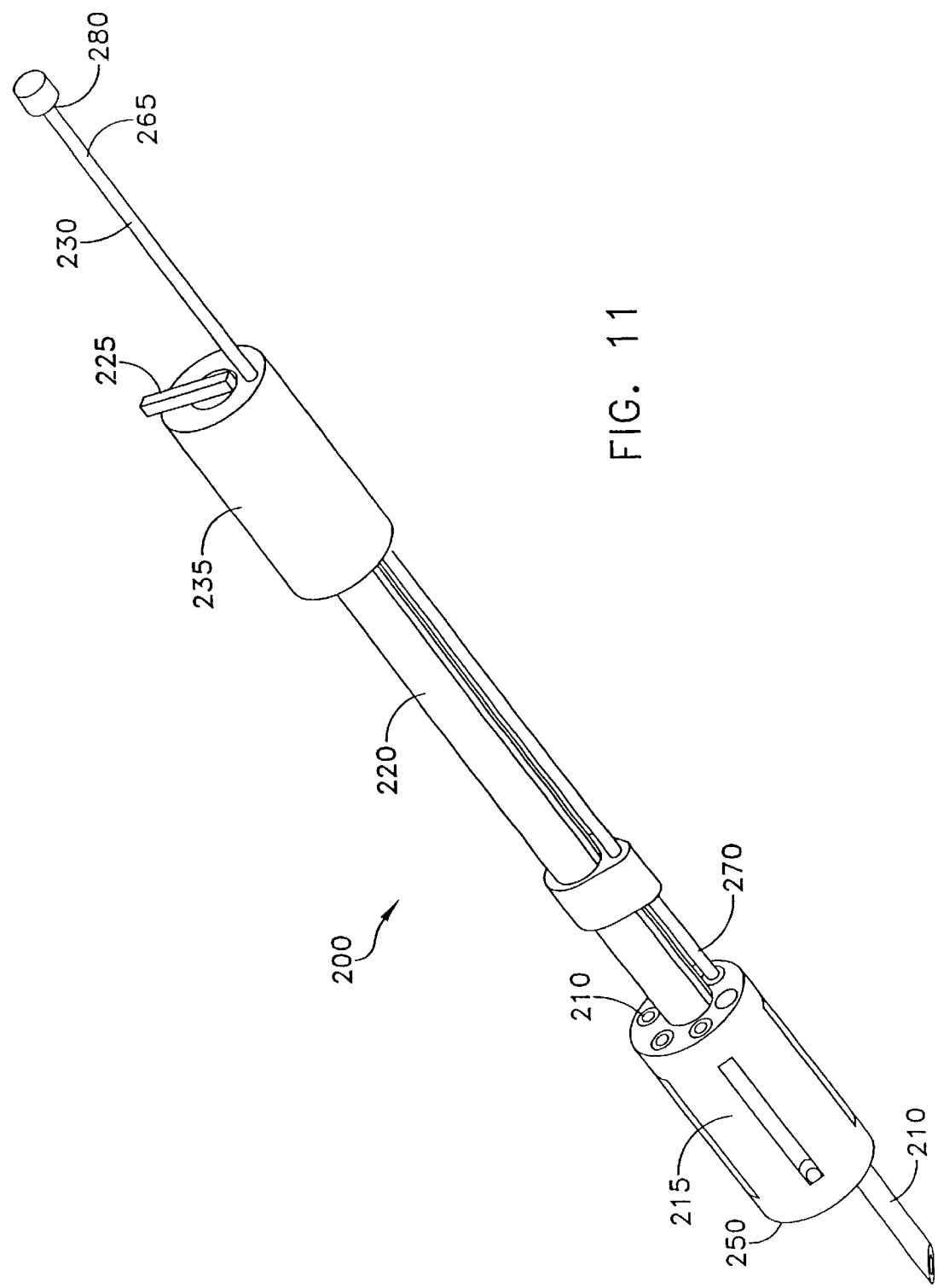
Figure 11A:
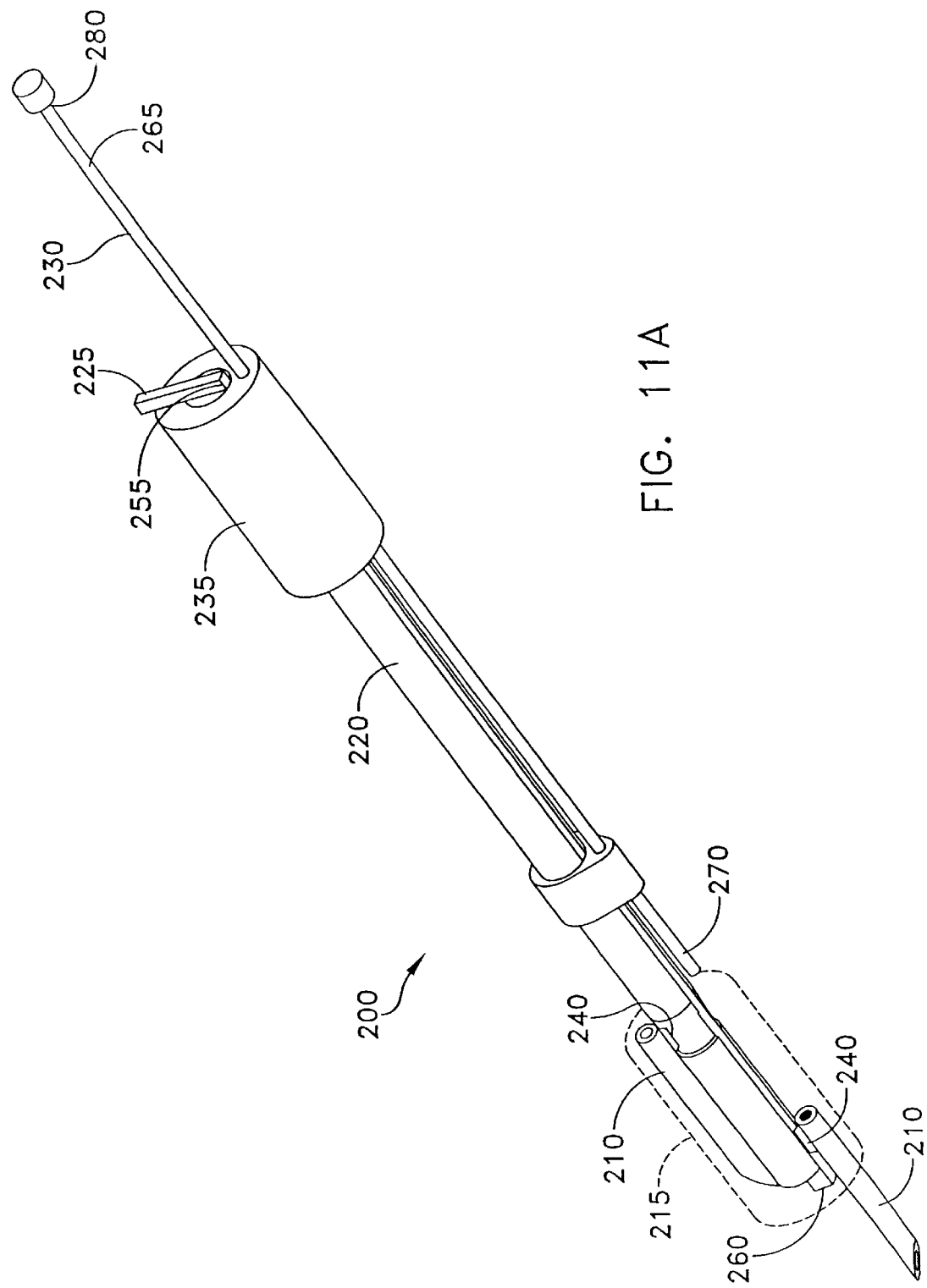
Figure 12:
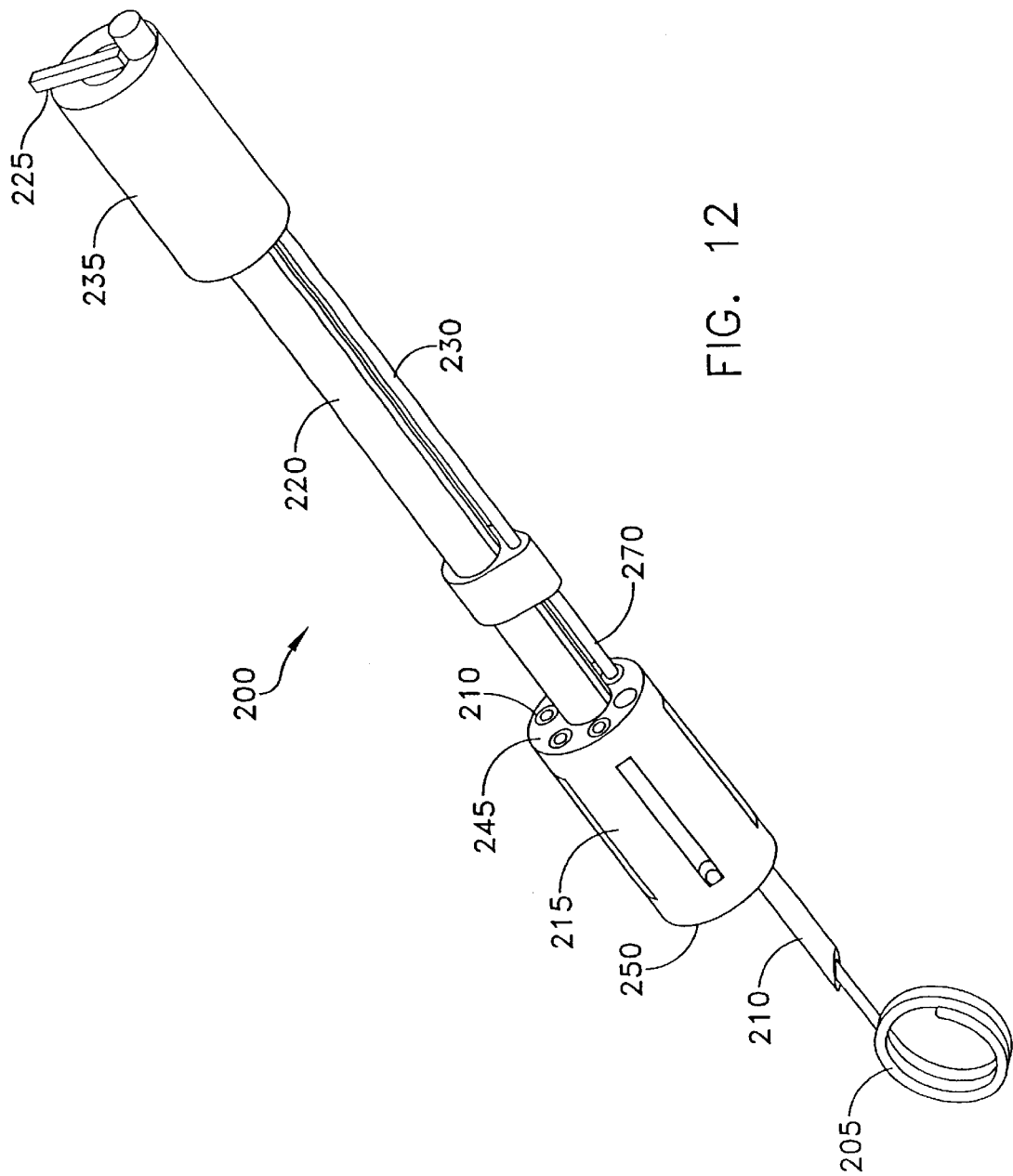
Figure 12A:
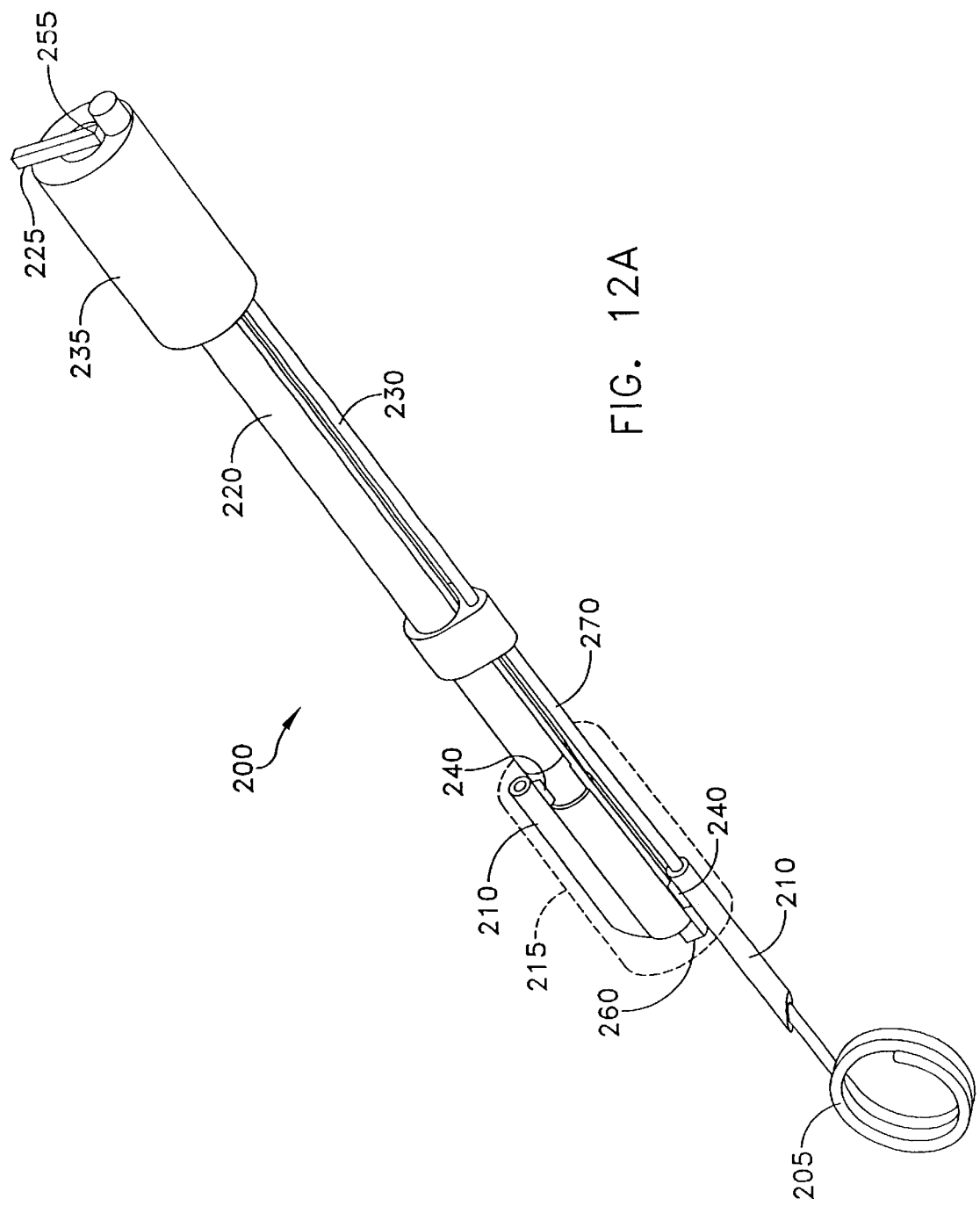

In FIGS. 10–12 (and FIGS. 10A–12A and 10B–12B), there is shown a multi-fastener surgical apparatus 200. Multi-fastener surgical apparatus 200 is configured to permit the sequential delivery of a series of surgical fasteners 205 without reloading after each placement. More particularly, multi-fastener surgical apparatus 200 includes at least two fasteners 205 provided in corresponding delivery tubes 210 of a cartridge 215. A body 220 is shown rotatably attached to cartridge 215 and a delivery tube control 225 is in selective engagement with sequential ones of the delivery tubes 210. A plunger 230 is adapted for selective end-to-end engagement with sequential ones of the surgical fasteners 205. A handle 235 is rotatably attached to body 220. Delivery tube control 225 and plunger 230 are each slidably connected to handle 235.

Still looking at FIGS. 10–12 (and FIGS. 10A–12A and 10B–12B), delivery tubes 210 are slidably disposed within cartridge 215, in a surrounding configuration to body 220. In a preferred embodiment of the invention, six to eight delivery tubes 210 are provided, each delivery tube containing a preformed fastener 205 held in a substantially linear configuration, in the manner previously described. Each of the delivery tubes 210 has a proximal end 245 and a distal end 250. In a preferred embodiment of the present invention, proximal end 245 is shown having a flange 240 for selective engagement by delivery tube control 225. Distal ends 250 are shown sharpened with a cutting edge for penetration through the material (not shown) which is to be joined. In an alternative embodiment of the present invention, surgical fasteners 205 have a sharpened end (not shown) to penetrate the material (not shown) which is to be joined.

Still referring to FIGS. 10–12 (and FIGS. 10A–12A and 10B–12B), cartridge 215 is rotatably connected to handle 235 by body 220. Delivery tube control 225 and plunger 230 are slidably connected to handle 235. Delivery tube control 225 is shown having a proximal end 255 and a distal end 260. Plunger 230 is shown having a proximal end 265 and a distal end 270. A first stop 275 is formed on the proximal end 255 of delivery tube control 225, and a second stop 280 is formed on the proximal end 265 of plunger 230. First stop 275 limits the distal movement of delivery tube control 225, which in turn limits the distal penetration depth of delivery tube 210 as it advances from cartridge 215. Second stop 280 limits the distal movement of plunger 230, which in turn limits the length of surgical fastener 205 advanced out of delivery tube 210 by plunger 230.

Rotation of cartridge 215 with respect to handle 235 aligns a subsequent delivery tube 210 and surgical fastener 205 with the distal end 260 of delivery tube control 225 and the distal end 270 of plunger 230. This rotation occurs between placements of successive surgical fasteners 205. If desired, this rotation may be automatically effected with mechanical elements after plunger 230 is inserted and withdrawn from delivery tube 210, in the manner similar to the cylinder of a revolver pistol. Alternatively, rotation may be accomplished by manually turning cartridge 215 with respect to handle 235.

Figure 13:
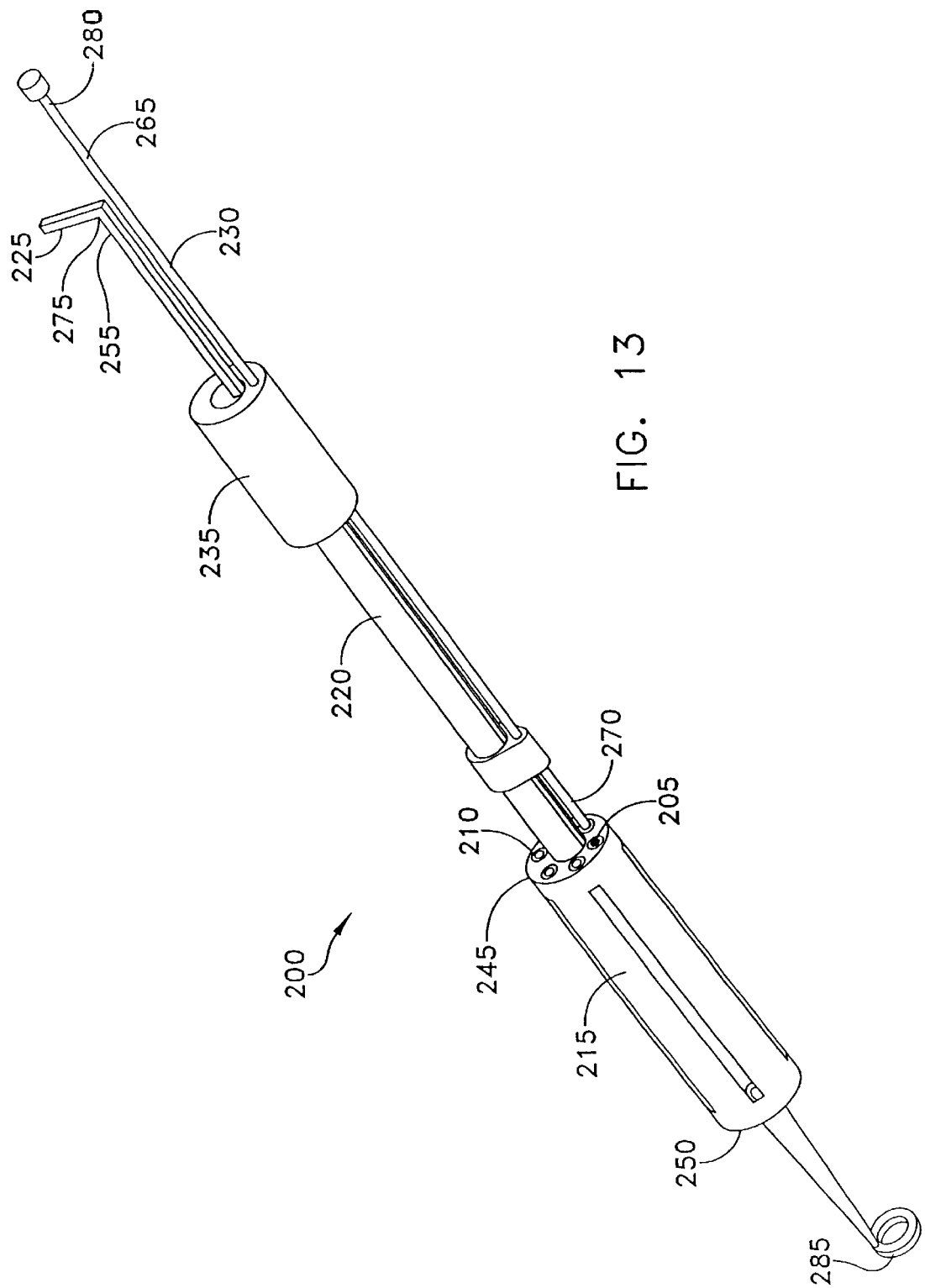
FIGS. 13–15 are perspective views showing use of an alternative form of multi-suture deployment apparatus with the surgical fastener of FIG. 2.
Figure 13A:
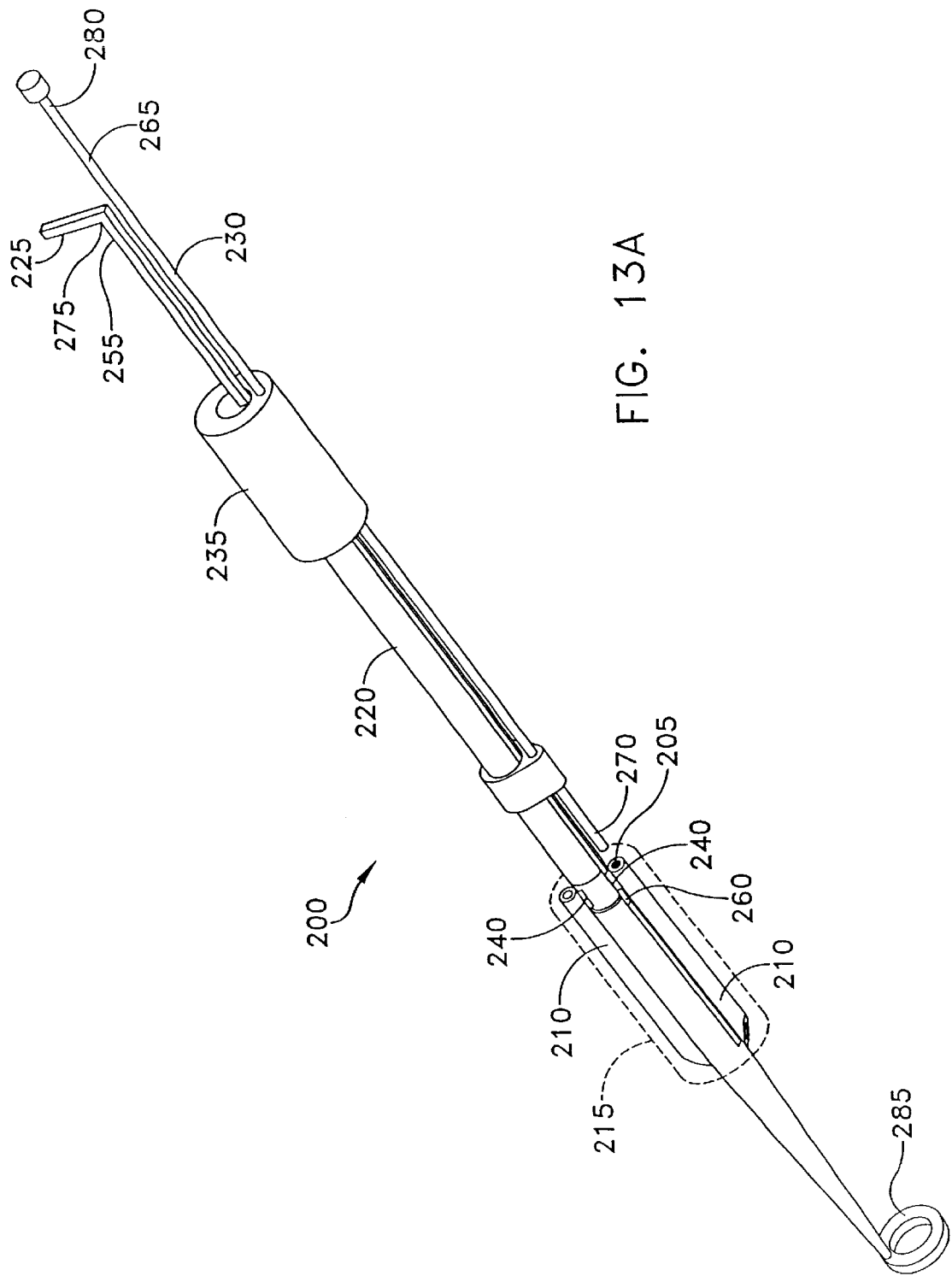
Figures 13B, 14B, 15B:
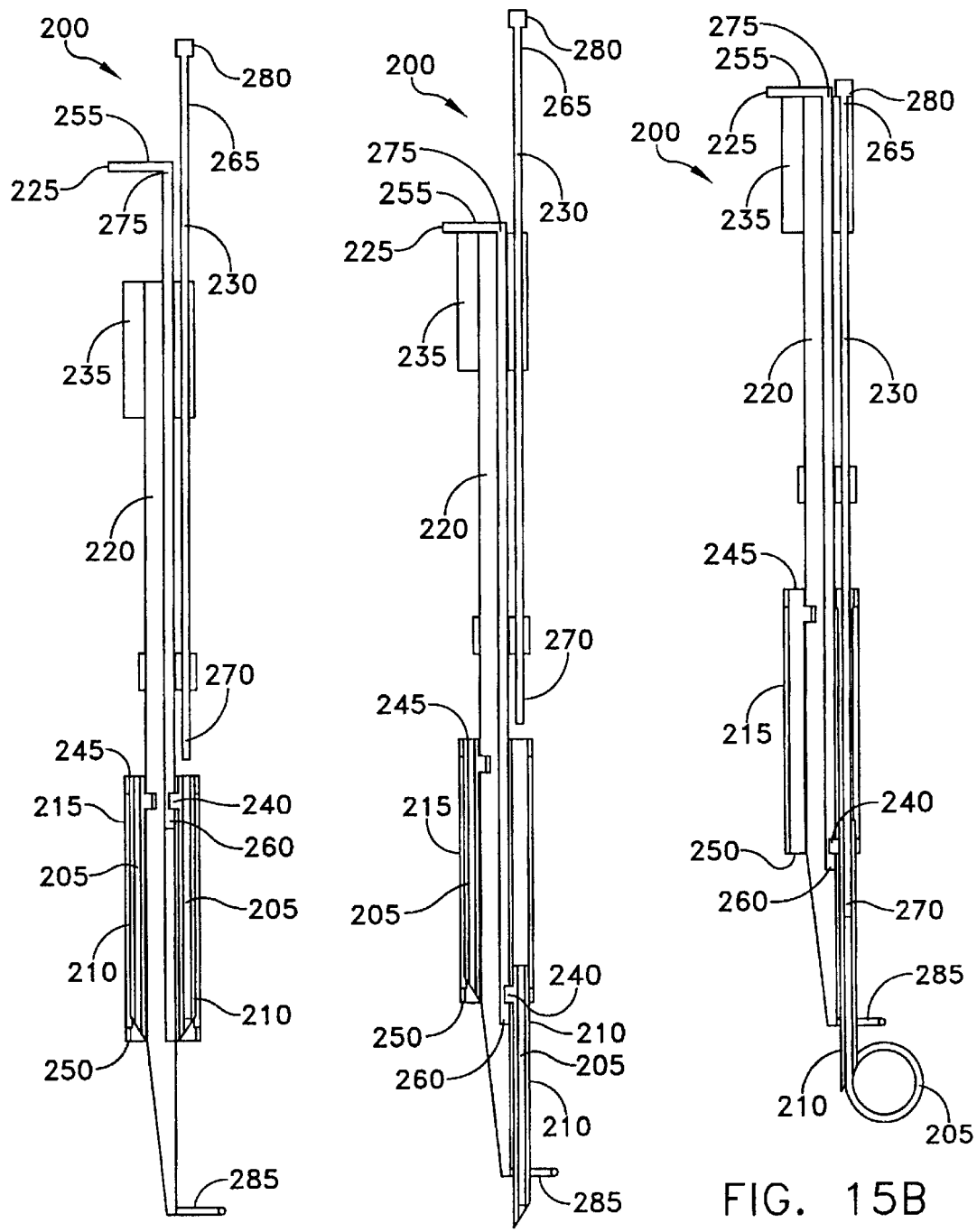
Figure 14:
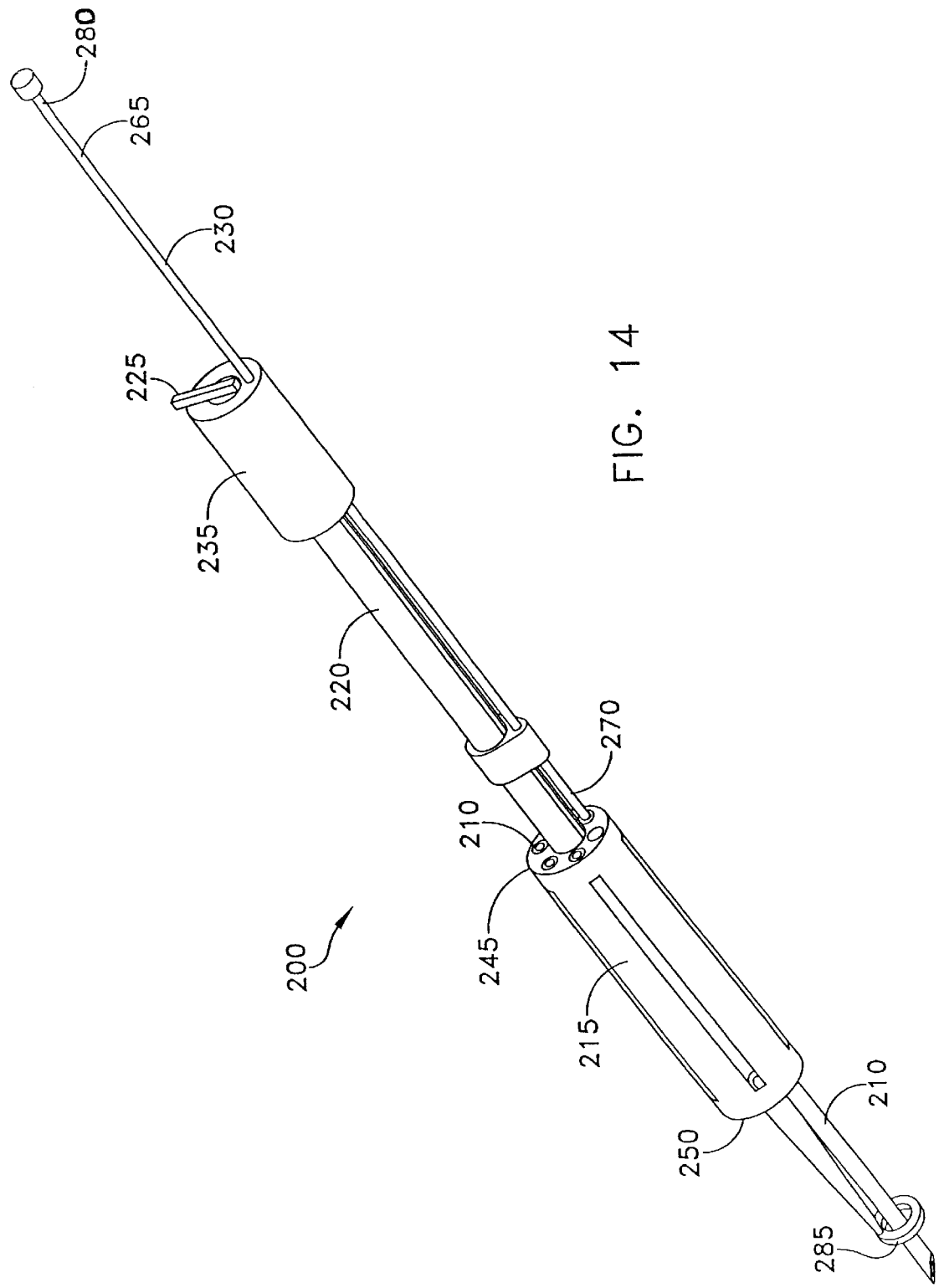
Figure 14A:
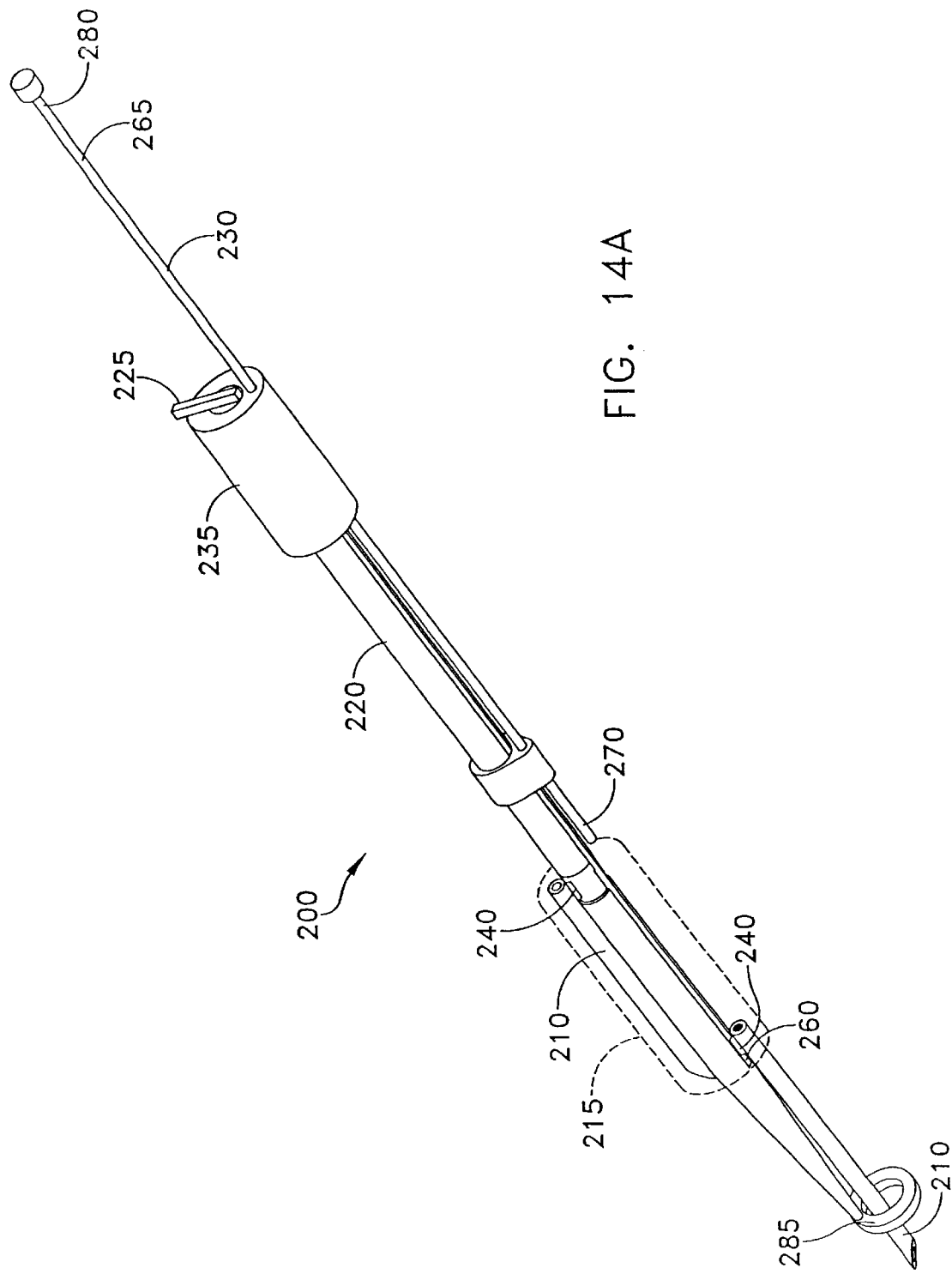
Figure 15:
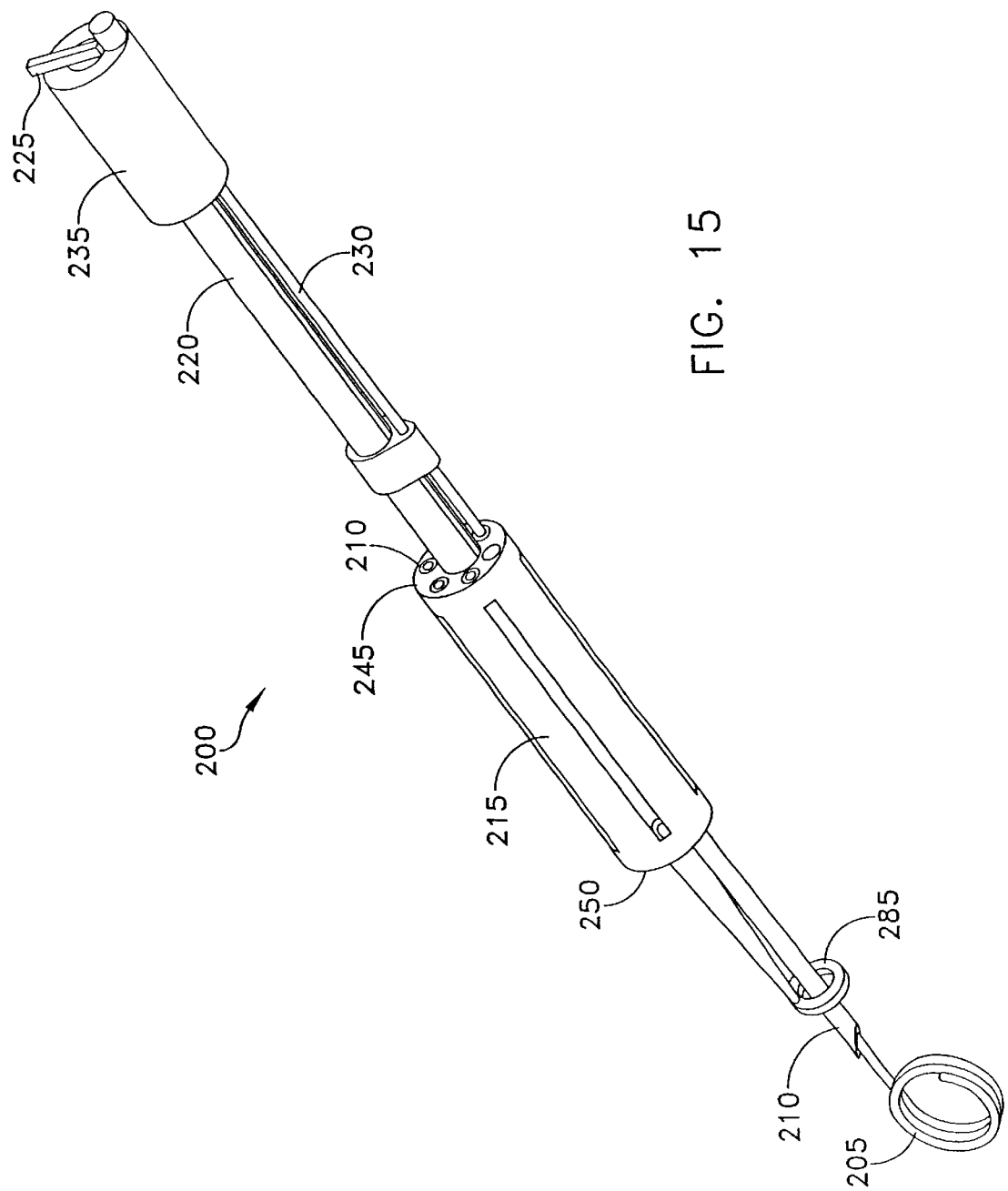

Looking next at FIGS. 13–15 (and FIGS. 13A–15A and 13B–15B), it will be seen that body 220 may be extended distally so as to provide a circular foot 285. Circular foot 285 can be positioned on the distal side of the tissue which is to be joined, such that the circular foot 285 can provide support for the tissue during penetration of the tissue by a delivery tube 210.

Figure 16:
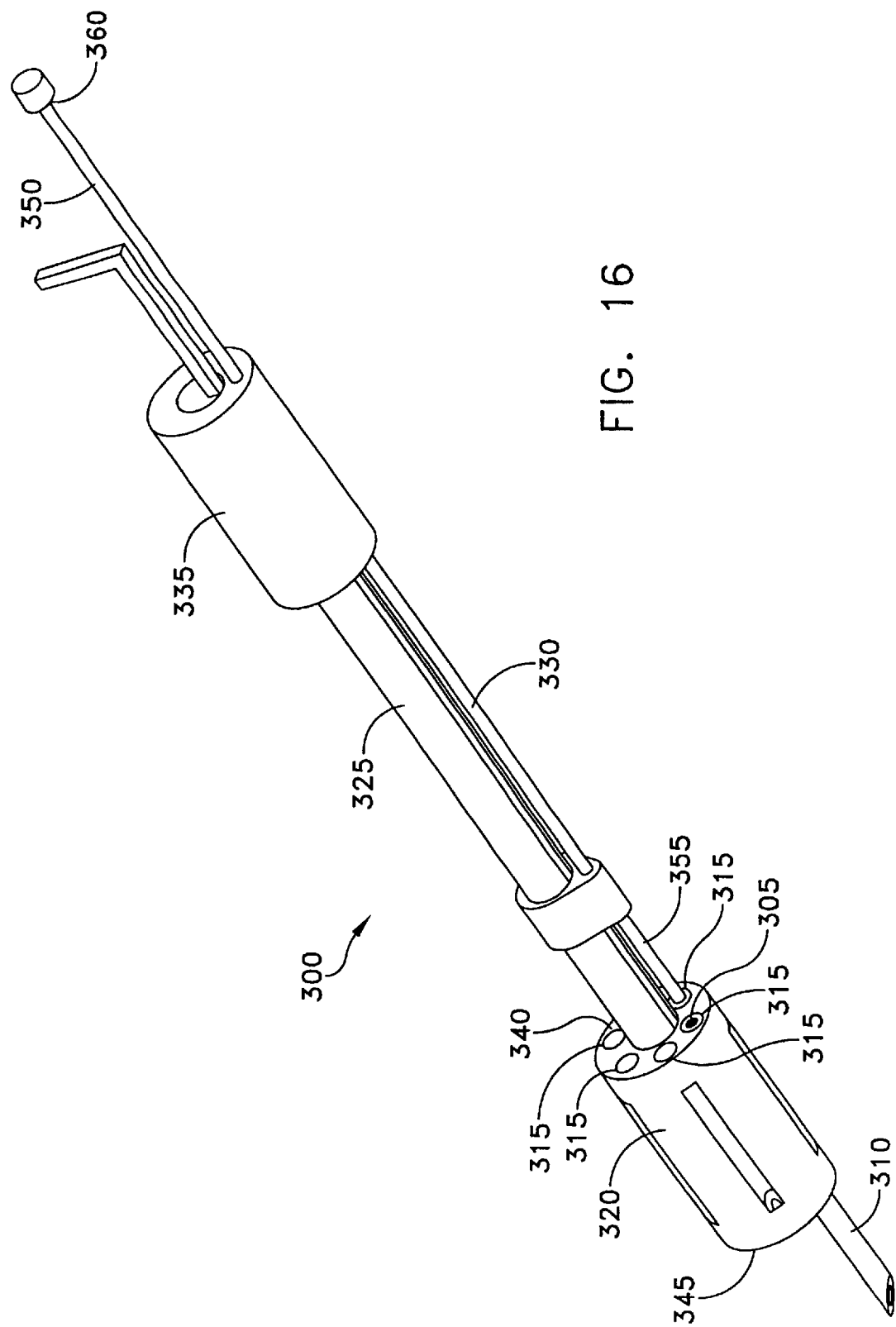
FIGS. 16–18 are perspective views showing another alternative form of multi-suture deployment apparatus.
Figure 17:
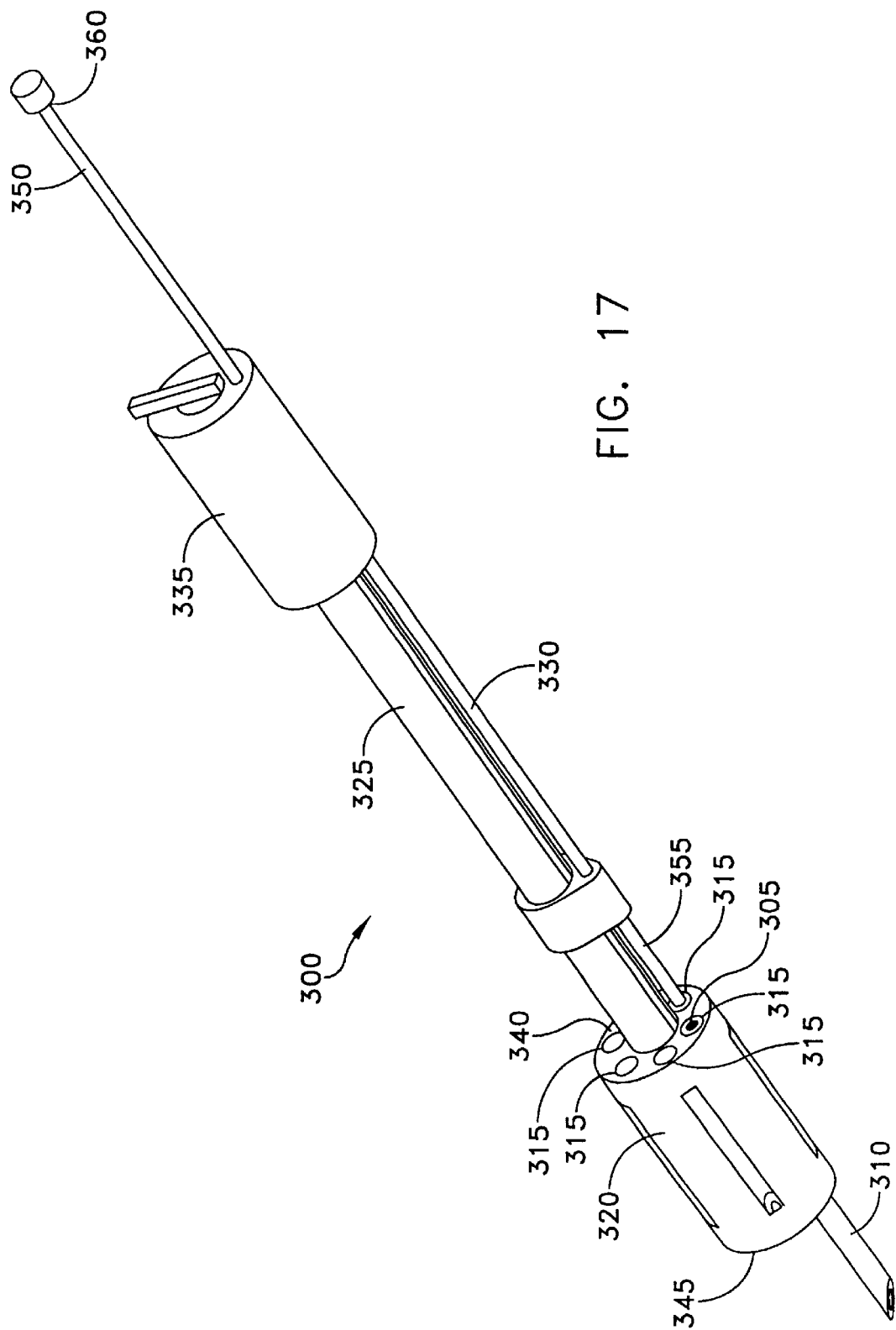
Figure 18:
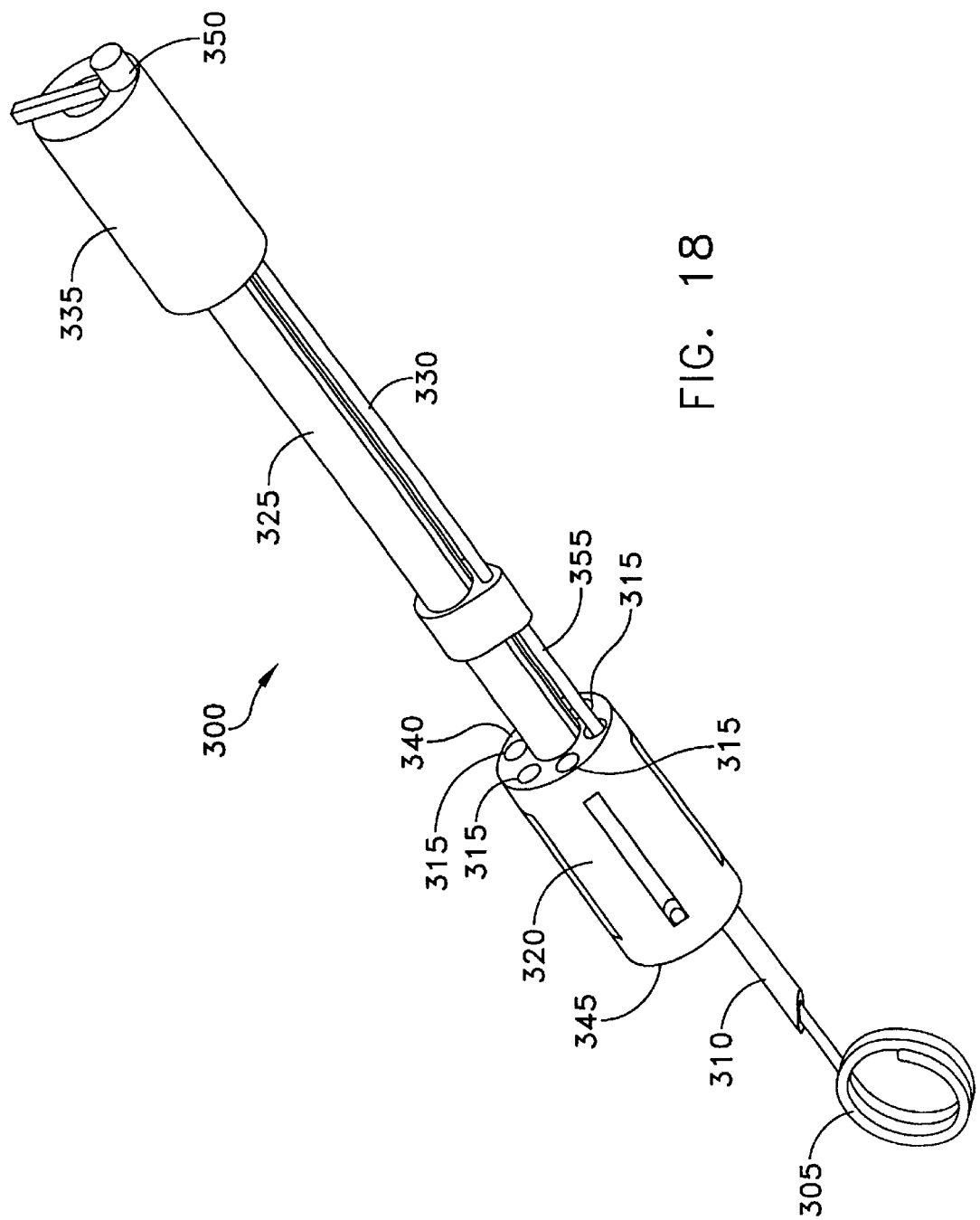

Looking next at FIGS. 16–18, there is shown a single-needle multi-fastener surgical apparatus 300. Single-needle multi-fastener surgical apparatus 300 is configured to permit the sequential delivery of a series of surgical fasteners 305 placed through a single needle 310 without reloading after placement. More particularly, a series of cylindrical openings 315 formed in cartridge 320 each contain a single surgical fastener 305. Cartridge 320 is rotatably attached to body 325. Body 325 is fixedly attached to single needle 310. A plunger 330 is shown in selective end-to-end engagement with sequential ones of surgical fasteners 305. A handle 335 is shown in attachment with body 325. Plunger 330 is slidably attached to handle 335.

Still looking at FIGS. 16–18, the series of cylindrical openings 315 are disposed in a surrounding configuration to body 325. In a preferred embodiment of the invention, six to eight cylindrical openings 315 are provided, and each one contains a preformed fastener 305 held in a substantially linear configuration, in the manner previously described. Each of the cylindrical openings 315 have a proximal end 340 and a distal end 345.

Cartridge 320 is rotably connected to handle 335 and single needle 310 by body 325. Plunger 330 is slidably connected to handle 335. Plunger 330 has a proximal end 350 and a distal end 355. In a preferred embodiment of the invention, a stop 360 is shown at the proximal end 350 of plunger 330. Stop 360 limits the distal movement of plunger 330, which in turn limits the distal penetration of surgical fastener 305 from single needle 310. As plunger 330 limits the distal penetration of surgical fastener 305 prior to withdrawal of single needle 310, a portion of surgical fastener 305 will remain on the proximal side of the tissue (not shown).

Rotation of cartridge 320 with respect to handle 335 aligns a cylindrical opening 315 and surgical fastener 305 with the distal end 355 of plunger 330. This rotation occurs between placement of successive surgical fasteners 305. This rotation may be effected automatically after plunger 330 is inserted and withdrawn from cylindrical opening 315, in the manner of the cylinder in a revolver pistol. Alternatively, rotation may be accomplished by manually turning cartridge 320 with respect to handle 335.

Figure 19:
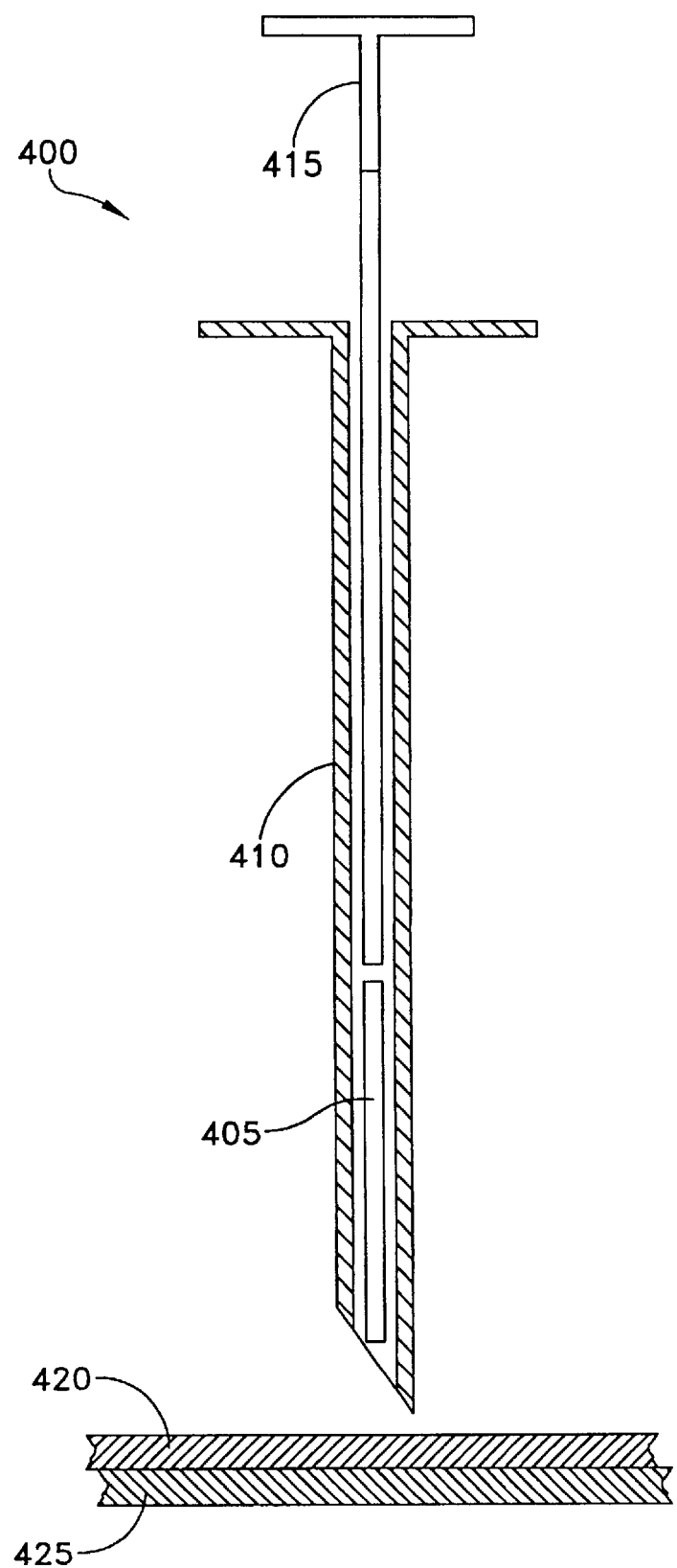
FIGS. 19–21 are side views showing use of a single suture deployment apparatus with the surgical apparatus of FIG. 2.
Figure 20:
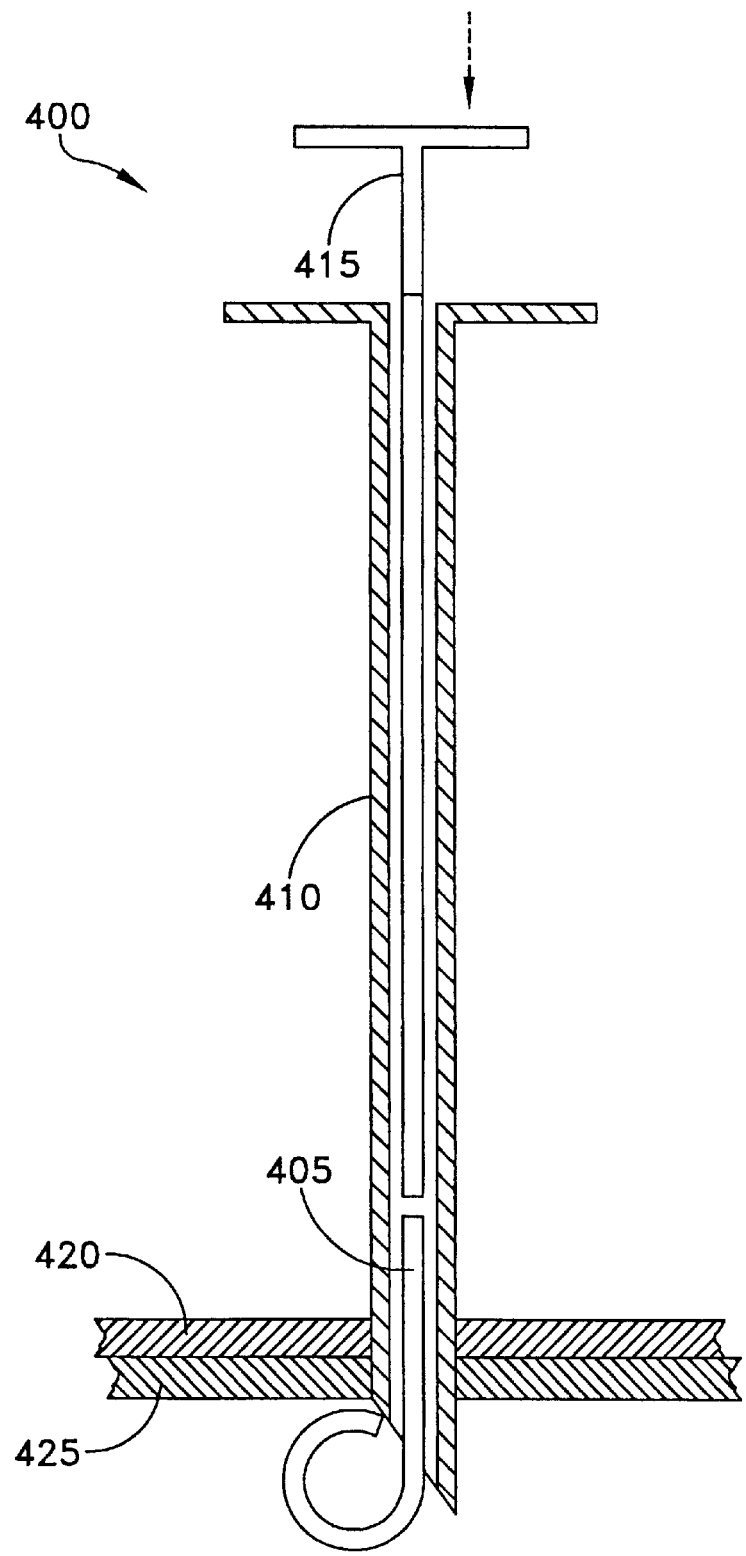
Figure 21:
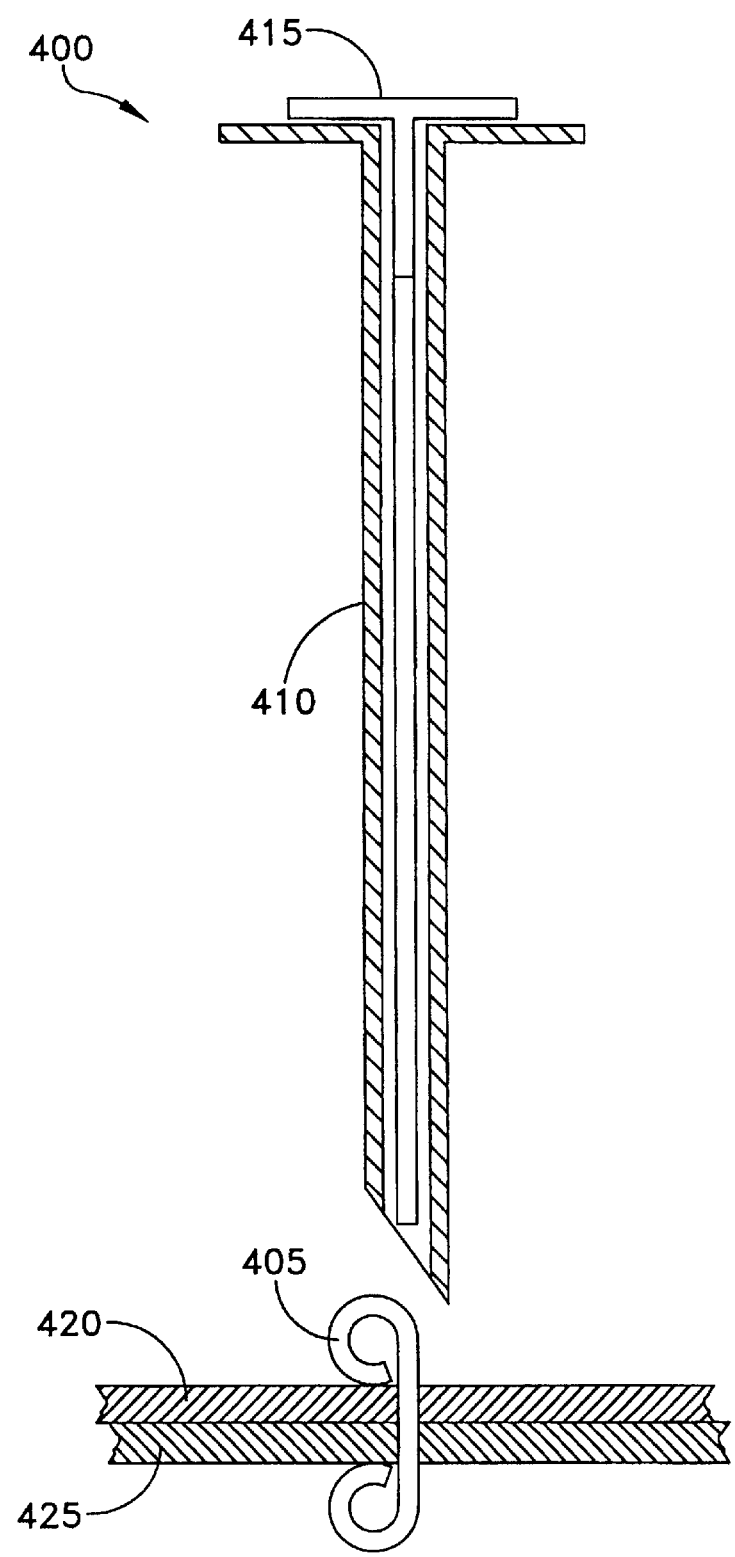

Looking next at FIGS. 19–21, there is shown a single-needle surgical apparatus 400. Single needle surgical apparatus 400 is configured to deliver a preloaded surgical fastener 405 through a single needle 410. A plunger 415 ejects surgical fastener 405 from the needle.

Single-needle surgical apparatus 400 is used to join two portions 420, 425 of material together with surgical fastener 405 by placing the distal end of single needle 410 at a desired location. Next, the distal end of plunger 415 is advanced distally so as to deploy a portion of the fastener 405 on the distal side of portions 420, 425. Single needle 410 is then withdrawn proximally from the material 420, 425 and then plunger 415 may be advanced further distally, such that the remaining portion of the surgical fastener 405 is ejected from needle 410, whereby to join the two portions of material together.

It should be appreciated that the apparatus described above may be used to attach two or more segments together, e.g., tissue to tissue, prosthesis to tissue, etc. In this respect it should also be appreciated that the apparatus may be used to occlude a tubular structure (e.g., a blood vessel, a fallopian tube, etc.) by securing one lumen segment to a diametrically opposed lumen segment. Still other applications will be apparent to those skilled in the art in view of the present disclosure.

It should be understood that the foregoing is illustrative and not limiting and that modifications may be made by those skilled in the art without departing from the scope of the invention.

What is claimed is:

1. Apparatus for inserting a surgical fastener through a plurality of portions of material, said apparatus comprising:
    a surgical fastener having first and second ends and made from a material which enables said fastener to be transformed from a first stressed elongate shape to a second unstressed shape upon release of said fastener from a stressed condition, the first stressed elongate shape of said fastener enabling the first end to be extended through a plurality of layers of material, and with the second shape of the fastener being in the form of a spring with a plurality of coils around a spring axis, with the coils being spring biased towards each other along the spring axis with sufficient axial force to enable the coils on opposite sides of the layers of material to clamp the layers of material together along the spring axis;
    a single needle having first and second ends,
    penetration means adjacent the first end of said single needle, said penetration means being configured to pierce through the plurality of layers of material, and insertion means adjacent to the first end of said single needle, said insertion means being configured to place said surgical fastener through the plurality of layers of material pierced by said penetration means;
    wherein said insertion means comprises a magazine comprising a plurality of chambers, with each chamber adapted to hold a fastener therein, and means for moving the magazine so as to sequentially align one of said chambers with said needle.

2. Apparatus for inserting multiple surgical fasteners through a plurality of portions of material, said apparatus comprising:
    a plurality of surgical fasteners, each of said surgical fasteners having first and second ends and made from a material which enables said fastener to be transformed from a first stressed elongate shape to a second unstressed shape upon the-release of said fastener from a stressed condition, said first stressed elongate shape of said fastener enabling said first end to be extended through a plurality of layers of material, and with said second shape of the fastener being in the form of a spring with a plurality of coils around a spring axis, with said coils being spring biased towards each other along said spring axis with sufficient axial force so as to enable coils on opposite sides of layers to clamp the layers of material together along the spring axis;
    a cartridge having a plurality of delivery tubes, said cartridge having first and second ends, each of said delivery tubes adapted to hold one of said surgical fasteners therein, each of said delivery tubes having first and second ends, said first end of said delivery tubes adapted to be slideably disposed from said first end of said cartridge, said first end of each of said delivery tubes having penetrating means to pierce through the plurality of layers of material;
    a body in adjustable connection to said cartridge, said body having delivery tube control means and surgical fastener insertion means, said delivery tube control means being adapted to move said first end of each of said delivery tubes through said first end of said cartridge to pierce through the plurality of layers of material, said surgical fastener insertion means being adapted to place said surgical fastener through the plurality of layers of material pierced by said penetrating means of each of said delivery tubes; and means for moving said cartridge with respect to said body to sequentially align one of said delivery tubes having one of said surgical fasteners of said cartridge with said delivery tube control means and said surgical fastener insertion means of said body, wherein said plurality of surgical fasteners is sequentially placed without reloading after each placement.

3. A method for inserting a surgical fastener through a plurality of portion of material, said method comprising:
providing apparatus for inserting multiple surgical fasteners through a plurality of portions of material, said apparatus comprising:
a plurality of surgical fasteners, each of said surgical fasteners having first and second ends and made from a material which enables said fastener to be transformed from a first stressed elongate shape to a second unstressed shape upon the release of said fastener from a stressed condition, said first stressed elongate shape of said fastener enabling said first end to be extended through a plurality of layers of material, and with said second shape of the element being in the form of a spring with a plurality of coils around a spring axis, with said coils being spring biased towards each other along said spring axis with sufficient axial force so as to enable coils on opposite sides of layers to clamp the layers of material together along spring axis;
a cartridge having a plurality of delivery tubes, said cartridge having first and second ends, each of said delivery tubes adapted to hold one of said surgical fasteners therein, each of said delivery tubes having first and second ends, said first end of said delivery tubes adapted to be slideably disposed from said first end of said cartridge, said first end of each of said delivery tubes having penetrating means to pierce through the plurality of layers of material;
a body in adjustable connection to said cartridge, said body having delivery tube control means and surgical fastener insertion means, said delivery tube control means being adapted to move said first end of each of said delivery tubes through said first end of said cartridge to pierce through the plurality of layers of material, said surgical fastener insertion means being adapted to place said surgical fastener through the plurality of layers of material pierced by said penetrating means of each of said delivery tubes; and
means for moving said cartridge with respect to said body to sequentially align one of said delivery tubes having one of said surgical fasteners of said cartridge with said delivery tube control means and said surgical fastener insertion means of said body, wherein said plurality of surgical fasteners is sequentially placed without reloading after each placement;
placing said first end of said cartridge adjacent the plurality of layers of material, with said surgical fastener being configured in said first elongate shape;
penetrating the plurality of layers of material with said first end of said delivery tube using said delivery tube control means;
inserting a first portion of said surgical fastener through the plurality of layers of material using said surgical fastener insertion means;
withdrawing said first end of said cartridge from the plurality of layers of material using said delivery control means; and
moving said cartridge with respect to said body to sequentially align said delivery tubes having one of said surgical fasteners of said cartridge with said delivery tube control means and said surgical fastener insertion means of said body, wherein said plurality of surgical fasteners are sequentially placed without reloading after each placement.

4. A method for inserting a surgical fastener through a plurality of portions of material, said method comprising:
providing apparatus for inserting a surgical fastener through a plurality of portions of material, said apparatus comprising:
a surgical fastener having first and second ends and made from a material which enables said fastener to be transformed from a first stressed elongate shape to a second unstressed shape upon release of said fastener from a stressed condition, the first stressed elongate shape of said fastener enabling the first end to be extended through a plurality of layers of material, and with the second shape of the element being in the form of a spring with a plurality of coils around a spring axis, with the coils being spring biased towards each other along the spring axis with sufficient axial force to enable the coils on opposite sides of the layers of material to clamp the layers of material together along the spring axis; and
a single needle having first and second ends, penetration means adjacent the first end of said single needle, said penetration means being configured to pierce through the plurality of layers of material, and insertion means adjacent to the first end of said single needle, said insertion means being configured to place said surgical fastener through the plurality of layers of material pierced by said penetration means;
placing said single needle adjacent the plurality of layers of material, with said surgical fastener being configured in the first stressed elongate shape;
penetrating the plurality of layers of material with said penetration means of said single needle, said penetration of the plurality of layers of material being performed at the first end of said single needle;
inserting a first portion of said surgical fastener through the plurality of layers of material using said insertion means; and
withdrawing said penetration means of said single needle from the plurality of layers of material, wherein a second portion of said surgical fastener is positioned on the opposite side of the plurality of layers of material from said first portion of said surgical fastener so as to enable the coils on the opposite sides of the layers to clamp the material together;
wherein one of said plurality of portions of surgical fastener comprises a lumen segment and the other of said plurality of portions of surgical fastener comprises another lumen segment.

5. A method according to claim 4 wherein said surgical fastener occludes the lumen upon deployment of said surgical fastener.

* * * * *